US011883268B2

(12) United States Patent
Johnson et al.

(10) Patent No.: US 11,883,268 B2
(45) Date of Patent: *Jan. 30, 2024

(54) FRONT OR REAR OPENING CLOSED-SIDED ABSORBENT ARTICLES

(71) Applicant: Kimberly-Clark Worldwide, Inc., Neenah, WI (US)

(72) Inventors: Beth Johnson, Appleton, WI (US); Sarah Kleuskens, Neenah, WI (US); James R Niedt, Grand Chute, WI (US); Kyle M Barriger, Neenah, WI (US); Marc A Morin, Jr., Appleton, WI (US); Thomas A Ray, Oshkosh, WI (US); Timothy A. Thorson, Neenah, WI (US); Victor Stevens, Cape Town (ZA)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1365 days.

This patent is subject to a terminal disclaimer.

(21) Appl. No.: 16/330,896

(22) PCT Filed: May 23, 2018

(86) PCT No.: PCT/US2018/034058
§ 371 (c)(1),
(2) Date: Mar. 6, 2019

(87) PCT Pub. No.: WO2018/222453
PCT Pub. Date: Dec. 6, 2018

(65) Prior Publication Data
US 2019/0209392 A1    Jul. 11, 2019

Related U.S. Application Data

(60) Provisional application No. 62/512,925, filed on May 31, 2017.

(51) Int. Cl.
*A61F 13/49* (2006.01)
*A61F 13/84* (2006.01)
(Continued)

(52) U.S. Cl.
CPC ............ *A61F 13/49* (2013.01); *A61F 13/496* (2013.01); *A61F 13/64* (2013.01); *A61F 13/84* (2013.01);
(Continued)

(58) Field of Classification Search
CPC ........ A61F 13/496; A61F 13/49; A61F 13/64; A61F 13/84; A61F 2013/49063; A61F 2013/49087; A61F 2013/585
See application file for complete search history.

(56) References Cited

U.S. PATENT DOCUMENTS 4,522,874 A    6/1985  Pommez
4,610,680 A    9/1986  LaFleur
(Continued)

FOREIGN PATENT DOCUMENTS

CN    1210710 A    3/1999
CN    1933797 A    3/2007
(Continued)

*Primary Examiner* — Michele Kidwell
(74) *Attorney, Agent, or Firm* — KIMBERLY-CLARK WORLDWIDE, INC.

(57) ABSTRACT

Absorbent articles with front and rear opening features are disclosed. An article may comprise an insert comprising an outer cover, a liner, and a core between the outer cover and liner, a first waist panel coupled to the insert throughout a first attachment region, and a second waist panel coupled to the insert throughout a second attachment region, the second panel being coupled to the first panel proximate a first side edge of the article and the second side edge of the article and further comprising a weakened region. The second attachment may comprise a low-strength attachment zone and a
(Continued)

high-strength attachment zone, the high-strength attachment zone disposed proximate the attachment region bottom edge. The low-strength attachment zone may further have a first peel strength and the high-strength attachment zone may have a second peel strength, the second peel strength greater than the first.

19 Claims, 10 Drawing Sheets

(51) Int. Cl.
*A61F 13/496* (2006.01)
*A61F 13/64* (2006.01)
*A61F 13/15* (2006.01)
*A61F 13/58* (2006.01)

(52) U.S. Cl.
CPC ............... *A61F 2013/15569* (2013.01); *A61F 2013/49063* (2013.01); *A61F 2013/49087* (2013.01); *A61F 2013/585* (2013.01)

(56) References Cited

U.S. PATENT DOCUMENTS

| | | | |
|---|---|---|---|
| 4,619,649 | A | 10/1986 | Roberts |
| 4,743,239 | A | 5/1988 | Cole |
| 4,747,846 | A | 5/1988 | Boland et al. |
| 4,909,804 | A | 3/1990 | Douglas |
| 4,936,840 | A | 6/1990 | Proxmire |
| 5,163,932 | A | 11/1992 | Nomura et al. |
| 5,370,634 | A | 12/1994 | Ando et al. |
| H1420 | H | 2/1995 | Richardson |
| 5,601,543 | A | 2/1997 | Dreier et al. |
| 5,624,420 | A | 4/1997 | Bridges et al. |
| 5,626,574 | A | 5/1997 | Sasaki et al. |
| 5,662,641 | A | 9/1997 | Gulsby |
| D389,320 | S | 1/1998 | Vinnage et al. |
| 6,027,484 | A | 2/2000 | Romare |
| D422,698 | S | 4/2000 | Witsken |
| 6,213,991 | B1 | 4/2001 | Kling et al. |
| D445,897 | S | 7/2001 | Oberstadt |
| D445,898 | S | 7/2001 | Malchow et al. |
| D446,303 | S | 8/2001 | Glaug et al. |
| 6,302,871 | B1 | 10/2001 | Nakao et al. |
| 6,387,083 | B1 | 5/2002 | Suzuki |
| 6,508,797 | B1 | 1/2003 | Pozniak et al. |
| 6,554,816 | B1 | 4/2003 | Olson |
| 6,743,321 | B2 | 6/2004 | Guralski et al. |
| 6,755,808 | B2 | 6/2004 | Balogh et al. |
| 6,976,978 | B2 | 12/2005 | Ruman et al. |
| 7,077,834 | B2 | 7/2006 | Bishop et al. |
| 7,331,087 | B2 | 2/2008 | Lindsay et al. |
| 7,393,429 | B2 | 7/2008 | Tachibana |
| 7,438,709 | B2 | 10/2008 | Karami et al. |
| 7,473,818 | B2 | 1/2009 | Datta et al. |
| 7,608,068 | B2 | 10/2009 | Fujioka |
| 7,765,614 | B2 | 8/2010 | Takino et al. |
| 7,789,868 | B2 | 9/2010 | Tachibana |
| 7,883,498 | B2 | 2/2011 | Waksmundzki et al. |
| 7,964,276 | B2 | 6/2011 | Hall et al. |
| 7,988,682 | B2 | 8/2011 | Olsson et al. |
| 8,034,039 | B2 | 10/2011 | Nakaoka et al. |
| 8,066,687 | B2 | 11/2011 | Ashton et al. |
| 8,118,799 | B2 | 2/2012 | Datta et al. |
| 8,123,733 | B2 | 2/2012 | O |
| 8,197,458 | B2 | 6/2012 | Bäck |
| 8,257,335 | B2 | 9/2012 | LaVon et al. |
| 8,343,127 | B1 | 1/2013 | Dimitrijevs et al. |
| 8,449,519 | B2 | 5/2013 | Een et al. |
| 8,470,440 | B2 | 6/2013 | Dalal |
| 8,506,544 | B2 | 8/2013 | Ashton et al. |
| 8,632,516 | B2 | 1/2014 | Ashton et al. |
| 8,663,184 | B2 | 3/2014 | Liu et al. |
| 8,663,415 | B2 | 3/2014 | Thorson et al. |
| 8,992,496 | B2 | 3/2015 | Bäck |
| 2002/0095130 | A1 | 7/2002 | Seitter et al. |
| 2002/0111596 | A1 | 8/2002 | Fletcher et al. |
| 2003/0028166 | A1 | 2/2003 | Price et al. |
| 2003/0055389 | A1 | 3/2003 | Sanders et al. |
| 2004/0102757 | A1 | 5/2004 | Olson |
| 2004/0122404 | A1 | 6/2004 | Meyer et al. |
| 2004/0182502 | A1 | 9/2004 | Wagner et al. |
| 2004/0186451 | A1 | 9/2004 | Bishop et al. |
| 2005/0148965 | A1 | 7/2005 | Richlen et al. |
| 2005/0148974 | A1 | 7/2005 | Datta et al. |
| 2005/0177125 | A1 | 8/2005 | Kondo |
| 2005/0192553 | A1 | 9/2005 | Hasler et al. |
| 2005/0230313 | A1 | 10/2005 | John |
| 2005/0277905 | A1 | 12/2005 | Pedersen et al. |
| 2006/0052763 | A1 * | 3/2006 | Tachibana ......... A61F 13/15699 604/395 |
| 2006/0129119 | A1 | 6/2006 | Kistler |
| 2007/0049897 | A1 | 3/2007 | LaVon et al. |
| 2007/0287980 | A1 | 12/2007 | Kline et al. |
| 2008/0021424 | A1 | 1/2008 | Erdman |
| 2008/0021425 | A1 | 1/2008 | Nakaoka et al. |
| 2008/0045918 | A1 | 2/2008 | Driskell |
| 2008/0091163 | A1 | 4/2008 | Fujioka |
| 2008/0114322 | A1 | 5/2008 | Schmoker et al. |
| 2008/0134487 | A1 | 6/2008 | Hartono |
| 2008/0154223 | A1 | 6/2008 | Fujioka |
| 2008/0249493 | A1 | 10/2008 | Kobayashi et al. |
| 2009/0198207 | A1 | 8/2009 | Torigoshi et al. |
| 2010/0004616 | A1 | 1/2010 | Nakamura et al. |
| 2010/0234822 | A1 | 9/2010 | Bäck |
| 2011/0313382 | A1 | 12/2011 | Ashton et al. |
| 2012/0101468 | A1 | 4/2012 | Sperl |
| 2012/0157953 | A1 | 6/2012 | Ashton et al. |
| 2012/0157954 | A1 | 6/2012 | Ashton et al. |
| 2012/0253307 | A1 | 10/2012 | Takeuchi et al. |
| 2013/0158498 | A1 | 6/2013 | Clark, Jr. et al. |
| 2013/0317471 | A1 | 11/2013 | Morimoto et al. |
| 2014/0115757 | A1 | 5/2014 | Umebayashi |
| 2014/0135730 | A1 | 5/2014 | Mlinar et al. |
| 2014/0155855 | A1 | 6/2014 | Romzek et al. |
| 2017/0049639 | A1 | 2/2017 | Shimazu et al. |
| 2019/0365575 | A1 * | 12/2019 | Johnson ............ A61F 13/15723 |
| 2020/0163810 | A1 * | 5/2020 | Johnson ............ A61F 13/49011 |

FOREIGN PATENT DOCUMENTS

| | | |
|---|---|---|
| CN | 101155566 A | 4/2008 |
| CN | 101909568 A | 12/2010 |
| CN | 105188630 A | 12/2015 |
| CN | 106061448 A | 10/2016 |
| DE | 19813334 A1 | 9/1999 |
| EP | 0544703 B1 | 9/1994 |
| EP | 0570980 B1 | 7/1997 |
| EP | 1027874 A2 | 8/2000 |
| EP | 0975296 B1 | 12/2004 |
| EP | 1682349 B1 | 4/2008 |
| JP | 5014452 A2 | 1/1993 |
| JP | 5342962 A2 | 12/1993 |
| JP | 6031721 U1 | 4/1994 |
| JP | 2000316900 A | 11/2000 |
| JP | 2005230313 A | 9/2005 |
| JP | 2006057208 A | 3/2006 |
| JP | 2007236434 A | 9/2007 |
| JP | 2008080024 A | 4/2008 |
| JP | 2008142345 A | 6/2008 |
| JP | 4181065 B2 | 11/2008 |
| JP | 4276556 B2 | 6/2009 |
| JP | 4508892 B2 | 7/2010 |
| JP | 4511284 B2 | 7/2010 |
| JP | 2011072429 A | 4/2011 |
| JP | 4801498 B2 | 10/2011 |
| JP | 5400556 B2 | 1/2014 |
| JP | 5568369 B2 | 8/2014 |
| JP | 2016123640 A | 7/2016 |
| JP | 2016193055 A | 11/2016 |
| KR | 20130138781 A | 12/2013 |
| KR | 101478864 B1 | 1/2015 |

(56) References Cited

FOREIGN PATENT DOCUMENTS

| | | | |
|---|---|---|---|
| RU | 2370250 | C2 | 10/2009 |
| WO | 8907897 | A1 | 9/1989 |
| WO | 04017882 | A2 | 3/2004 |
| WO | 06071285 | A1 | 7/2006 |
| WO | 07037391 | A1 | 4/2007 |
| WO | 10110203 | A1 | 9/2010 |
| WO | 11049536 | A1 | 4/2011 |
| WO | 11090001 | A1 | 7/2011 |
| WO | 2011125678 | A1 | 10/2011 |
| WO | 11156299 | A1 | 12/2011 |

* cited by examiner

FRONT OR REAR OPENING CLOSED-SIDED ABSORBENT ARTICLES

CROSS-REFERENCE TO RELATED APPLICATION

This application claims the benefit of U.S. Provisional Application No. 62/512,925, filed May 31, 2017.

TECHNICAL FIELD

The present disclosure is directed to closed-sided absorbent articles, and more particularly to closed-sided absorbent articles which may be opened from the front or back.

BACKGROUND OF THE DISCLOSURE

Continued wearing of an absorbent article after exudates have been insulted onto the absorbent article can lead to a few different undesirable effects. For example, prolonged wearing of the absorbent article that is retaining body exudates can increase the potential for skin irritation. In addition, continued wearing of such an absorbent article can also lead to an increased likelihood that the gasketing systems of the absorbent article become compromised. These undesirable effects can be more common with respect to semi-solid fecal material. Such fecal material can have difficulty penetrating the bodyside liner of the absorbent article, and tend to spread across the surface of the bodyside liner.

Both closed-sided absorbent article products, including baby and adult products, often referred to as training pants and pull-on diapers when referencing baby care absorbent articles, and more traditional open absorbent articles may work to retain such exudates until the articles are removed. Additionally, each style of absorbent article, closed-sided and open, may provide different benefits and disadvantages. For instance, the closed-sided articles utilize chassis designs that are modeled more after conventional underwear, which may provide enhanced fit. However, open absorbent articles may be easier to remove cleanly, as the product may be opened at the waist and folded to contain the bodily exudates. Closed-sided articles are generally removed by either sliding the article down the wearer, potentially contaminating the wearer's legs with bodily exudates, or by tearing the sides of the article. However, tearing open the sides of such articles may make folding the articles to contain the exudates and maintaining such a folded state difficult. Accordingly, closed-sided absorbent articles which may be removed in an easier manner and provide a better ability to be folded, and remain folded, to contain bodily exudates are desired.

SUMMARY OF THE DISCLOSURE

The absorbent articles disclosed herein are closed-sided articles designed to be easy to open and easy to fold and maintain a folded shape. In general, the absorbent articles disclosed herein are constructed so as to have a front waist panel or a rear waist panel that is removably attached to an absorbent insert and which includes a weakened region that is easy to tear open. Additional features of absorbent articles of the present disclosure will be set forth in the below description.

In a first embodiment, an absorbent article may include a front region, a crotch region, a rear region, and a first side edge and a second side edge and may further comprise an absorbent insert comprising an outer cover, a liner, and an absorbent core disposed between the outer cover and the liner, a first waist panel coupled to the absorbent insert throughout a first attachment region, and a second waist panel coupled to the absorbent insert throughout a second attachment region, the second waist panel being coupled to the first waist panel proximate the first side edge of the absorbent article and the second side edge of the absorbent article and further comprising a weakened region. The second attachment region may comprise an attachment region top edge, an attachment region bottom edge, attachment region longitudinal side edges, and an overall attachment region area, and may further comprise a low-strength attachment zone and a high-strength attachment zone, the high-strength attachment zone being disposed proximate the attachment region bottom edge. The low-strength attachment zone may have a first peel strength and the high-strength attachment zone may have a second peel strength, the second peel strength being greater than the first peel strength.

In a second embodiment, the second attachment region of the first embodiment may comprise a first adhesive disposed throughout the low-strength attachment zone.

In a third embodiment, the second attachment region of the second embodiment may comprise a second adhesive disposed throughout the high-strength attachment zone, and the second adhesive may be different than the first adhesive.

In a fourth embodiment, the first adhesive of the third embodiment may have a drop time of less than about 4 hours in the Static Shear Test Method, and the second adhesive may have a drop time of greater than or equal to about 4 hours in the Static Shear Test Method.

In a fifth embodiment, the first adhesive of any of the second through fourth embodiment may be disposed throughout at least a portion of the high-strength attachment zone.

In a six embodiment, the first adhesive of any of the second through fifth embodiments, may be disposed throughout the entire high-strength attachment zone.

In a seventh embodiment, the high strength attachment zone of any of the second through six embodiments may comprise of a plurality of bonds.

In an eighth embodiment, the bonded surface area of the bonds of the seventh embodiment within the high-strength attachment zone may comprise between about 25% and about 75% of the surface area of the high-strength attachment zone.

In a ninth embodiment, the first peel strength of any of the first through eighth embodiments may be less than or equal to about 4 N, according to the Angled Peel Test Method, and the second peel strength may be greater than or equal to about 8 N, according to the Angled Peel Test Method.

In a tenth embodiment, the high-strength attachment zone of any of the first through ninth embodiments may be disposed proximate one of the attachment region longitudinal side edges.

In an eleventh embodiment, the second attachment region of any of the first through tenth embodiments may comprise a first high-strength attachment zone and a second high-strength attachment zone, the first high-strength attachment zone disposed proximate a first attachment region longitudinal side edge and the second high-strength attachment zone disposed proximate a second attachment region longitudinal side edge.

In a twelfth embodiment, the attachment region bottom edge of any of the first through eleventh embodiments may further comprise at least one recess, wherein the at least one recess may comprise a first recess side edge, a second recess side edge, and a recessed edge, where the first recess side edge may be located a distance between 15% and 40% of the overall attachment region width from the first attachment region longitudinal side edge, and where the second recess side edge may be located a distance between 15% and 40% of the overall attachment region width from the second attachment region longitudinal side edge.

In a thirteenth embodiment, the second attachment region of any of the eleventh or twelfth embodiments may comprise a first high-strength attachment zone and a second high-strength attachment zone, the first high-strength attachment zone disposed proximate the attachment region bottom edge and the second high-strength attachment zone disposed proximate the attachment region top edge.

In a fourteenth embodiment, an absorbent article including front region, a crotch region, and a rear region, and having a first side edge and a second side edge may comprise an absorbent insert comprising an outer cover, a liner, and an absorbent core disposed between the outer cover and the liner, a first waist panel coupled to the absorbent insert throughout a first attachment region, and a second waist panel coupled to the absorbent insert throughout a second attachment region and comprising a weakened region, the second waist panel being coupled to the first waist panel proximate the first side edge of the absorbent article and the second side edge of the absorbent article. The second attachment region may comprise an attachment region top edge, an attachment region bottom edge, attachment region longitudinal side edges, and overall attachment region area and may further comprise an adhesive-less region extending in a longitudinal direction where the weakened region overlaps the adhesive-less region.

In a fifteenth embodiment, the adhesive-less region of the fourteenth embodiment may have an adhesive-less region width, the adhesive-less region width being between about 8 mm and about 22 mm.

In a sixteenth embodiment, the adhesive-less region of any of the fourteenth or fifteenth embodiments may have an adhesive-less region width, the adhesive-less region width being between about 12 mm and about 18 mm.

In a seventeenth embodiment, the second attachment region of any of the fourteenth through sixteenth embodiments may further comprise a low-strength attachment zone and a high-strength attachment zone, the high-strength attachment zone being disposed proximate the attachment region bottom edge, wherein a peel strength of the low-strength attachment zone is less than or equal to about 4 N, according to the Angled Peel Test Method, and wherein a peel strength of the high-strength attachment zone is greater than or equal to about 8 N, according to the Angled Peel Test Method.

In an eighteenth embodiment, an absorbent article including front region, a crotch region, and a rear region, an having a first side edge and a second side edge may comprise an absorbent insert comprising an outer cover, a liner, and an absorbent core disposed between the outer cover and the liner, a first waist panel coupled to the absorbent insert throughout a first attachment region, and a second waist panel coupled to the absorbent insert throughout a second attachment region and comprising a weakened region, the second waist panel being coupled to the first waist panel proximate the first side edge of the absorbent article and the second side edge of the absorbent article. The second attachment region may comprise an attachment region top edge, an attachment region bottom edge, attachment region longitudinal side edges, and overall attachment region area and may further comprise a low-strength attachment zone, a first high-strength attachment zone, and a second high-strength attachment zone, the first high-strength attachment zone and the second high-strength attachment zone each being disposed proximate the attachment region bottom edge and one of the attachment region longitudinal side edges. The low-strength attachment zone may have a first peel strength and the high-strength attachment zone may have a second peel strength where the second peel strength may be greater than the first peel strength. The first high-strength attachment zone and the second high-strength attachment zone may each have a high-strength attachment zone area that is between about 0.5% and about 10% of the overall attachment region area.

In a nineteenth embodiment, the peel strength of the low-strength attachment zone of the eighteenth embodiment may be between about 1.5 N and about 4 N, according to the Angled Peel Test Method.

In a twentieth embodiment, the peel strength of the high-strength attachment zone of any of the eighteenth or nineteenth embodiments may be greater than or equal to about 8 N, according to the Angled Peel Test Method.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The aspects of the disclosure may be further understood in consideration of the following detailed description of various embodiments in connection with the accompanying drawings, in which.

Figure 1:
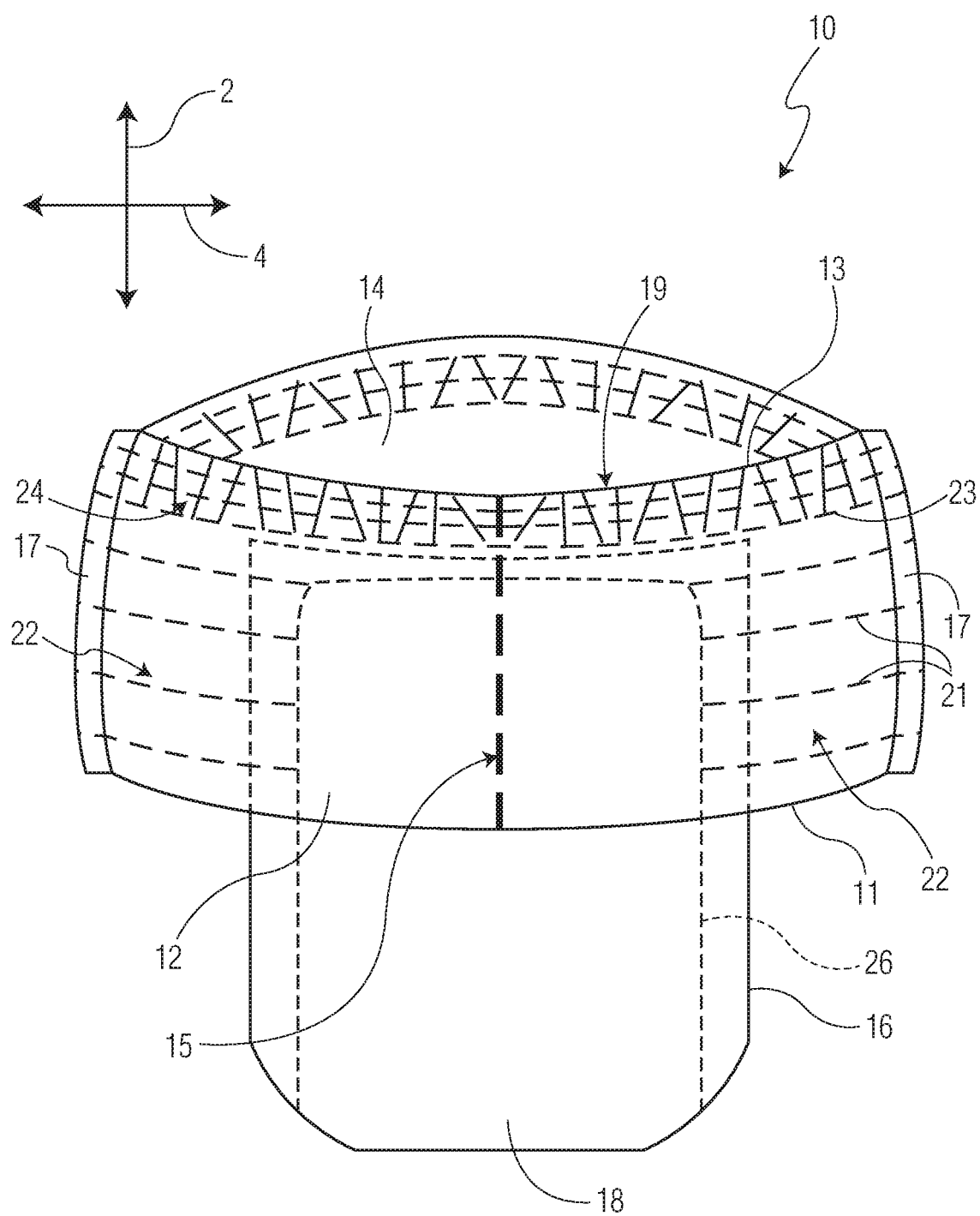
FIG. 1 is a perspective view of a disposable closed-sided absorbent article of the present disclosure in a wear configuration.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The present disclosure is generally directed towards closed-sided absorbent articles which may be opened from the front or from the back. More specifically, the articles of the present disclosure may have a front waist panel and a rear waist panel connected to an absorbent insert. At least one of the front waist panel and the rear waist panel may be releasably attached to the absorbent insert and may comprise a weakened region that is easy to tear-open. Accordingly, a user or caregiver may tear-open the absorbent article along the weakened region to allow for easy removal of the absorbent article from a wearer. Depending on the location of the weakened region, the closed-sided articles of the present disclosure may be opened from the front-side or the rear-side.

Each example in the following detailed description, including those examples shown in the different drawings, is provided by way of explanation and is not meant as a limitation. For example, features illustrated or described as part of one embodiment or figure can be used on another embodiment or figure to yield yet another embodiment, unless clearly stated to the contrary. It is intended that the present disclosure include such modifications and variations.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "light transmittance" or "light transmission" refers herein to a measured property of a substrate, or substrates, as defined by the Light Transmittance Test further described herein.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, training pant, youth pant, incontinent product, or other absorbent article about the wearer of one of these absorbent articles. A user and a wearer can be one and the same person.

Figure 3:
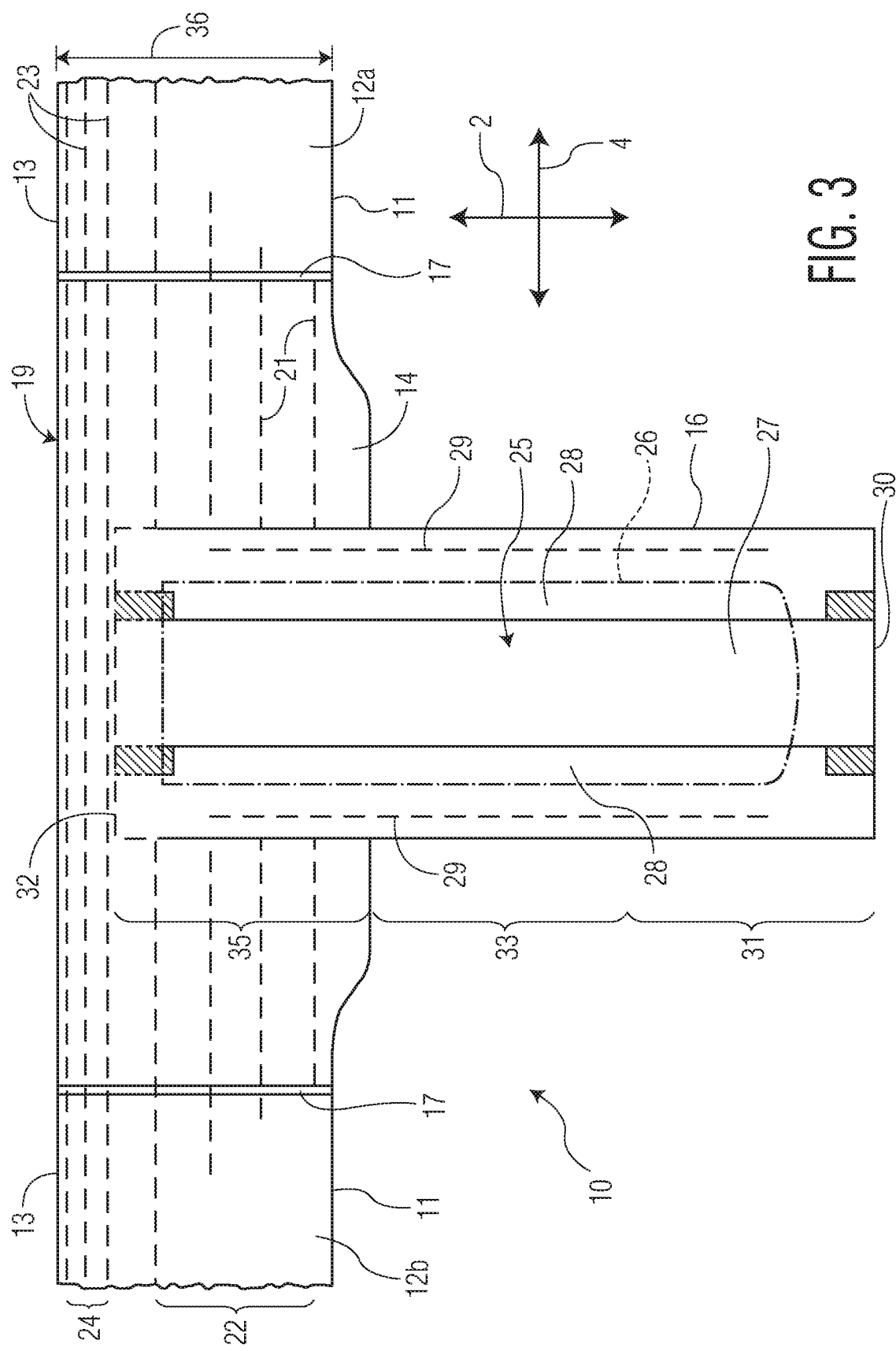
FIG. 3 is a plan view of the absorbent article of FIG. 1 in an open configuration.

FIG. 1 is a perspective view of a disposable closed-sided absorbent article 10 of the present disclosure in a wear configuration, and FIG. 3 is a plan view of the article 10 in an open configuration. In general, article 10 is a closed-sided absorbent article that may be used for children or adults. The article 10 can include a front waist panel 12 and a rear waist panel 14. The front waist panel 12 may be connected to the rear waist panel 14 along their lateral edges, for example by side-seam bonds 17, and may be separated from each other along their central regions. An absorbent insert 16 may span between, and connect to, the front waist panel 12 and the rear waist panel 14. As can be seen in FIG. 3, the absorbent insert 16 can include an insert front region 31 having an insert front edge 30, an insert crotch region 33, and an insert rear region 35 having an insert rear edge 32. In use, the insert front region 31 may be positioned on an anterior region of a wearer, while the insert rear region 35 may be positioned on a posterior region of the wearer. The insert crotch region 33 may be disposed at least partially between the legs of the wearer, and may even span portions of both the anterior region and posterior region of the wearer.

In general, the absorbent insert 16 may comprise of a plurality of different layers. For example, the absorbent insert 16 may comprise an outer cover 18, a bodyside liner 27, and an absorbent body disposed between the outer cover 18 and the bodyside liner 27. The outer cover 18, partially or wholly, can be breathable and/or liquid impermeable and at least some portions may be elastic, stretchable, or non-stretchable, in different embodiments. The outer cover 18 may be constructed of a single layer in some embodiments and multiple layers in other embodiments, for instance where the outer cover 18 comprises one or more laminates of materials. The outer cover 18 may comprise spunbond fabrics, films, meltblown fabrics, elastic netting, microporous webs, bonded-carded webs, and/or foams provided by elastomeric or polymeric materials.

In some contemplated embodiments, the outer cover 18 can be a single layer of a liquid impermeable material, such as a polymeric film. The outer cover 18 may be suitably stretchable, and more suitably elastic, in at least the lateral direction 4 of the absorbent article 10, and may be stretchable, and more suitably elastic, in both the lateral 4 and the longitudinal 2 directions. In further embodiments, the outer cover 18 can be a multi-layered laminate in which at least one of the layers is liquid impermeable. In some embodiments, the outer cover 18 can be a two-layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

In embodiments where the outer cover 18 includes multiple layers, the outer layer of the outer cover 18 can be any suitable material and may be one that provides a generally cloth-like texture or appearance to the wearer. One generic example of material suitable for use as an outer layer of an outer cover 18 can be an approximately 20 gsm spunbond polypropylene non-woven web. The outer layer may also be constructed of the same materials from which the bodyside liner 27 can be constructed, as described herein, and it also may be apertured to enhance evaporation of urine in the event the inner layer is vapor permeable. In some embodiments, the outer cover 18, or at least the outer layer of the outer cover 18 where the outer cover 18 is a multi-layer construction, can be embossed and/or matte finished to provide a more cloth-like texture or appearance.

At least one of the inner layers of the outer cover 18 (or the liquid impermeable outer cover 18 where the outer cover 18 is of a single-layer construction) is liquid impermeable and can be either vapor permeable (i.e., "breathable") or vapor impermeable. The liquid impermeable inner layer (or the liquid impermeable outer cover 18 where the outer cover 18 is of a single-layer construction) can be manufactured from a thin plastic film. The liquid impermeable inner layer (or the liquid impermeable outer cover 18 where the outer cover 18 is of a single-layer construction) can inhibit liquid body exudates from leaking out of the absorbent article 10 and wetting articles, such as bed sheets and clothing, as well as the wearer and caregiver. As some particular examples, the outer cover 18 can be constructed of a microporous polymeric film, such as polyethylene or polypropylene, or a non-woven material which has been coated or otherwise treated to impart a desired level of liquid impermeability.

The bodyside liner 27, shown in FIG. 3, of the absorbent article 10 can overlay the absorbent body 26 and the outer cover 18 and can isolate the wearer's skin from liquid waste retained by the absorbent body 26. In various embodiments, the absorbent insert 26 can further include a fluid transfer layer (not shown) and/or an acquisition layer (not shown), which would be positioned between the bodyside liner 27 and the absorbent body 26. In various embodiments, the bodyside liner 27 can be bonded to the acquisition layer and/or to the fluid transfer layer in different constructions, via adhesive and/or by a point fusion bonding. The point fusion bonding may be accomplished using ultrasonic, thermal, or pressure energy, and any combinations thereof.

In some embodiments, the bodyside liner 27 can extend beyond the absorbent body 26 to overlay a portion of the outer cover 18 and can be bonded thereto, to substantially enclose the absorbent body 26 between the outer cover 18 and the bodyside liner 27. It is contemplated that the bodyside liner 27 may be narrower than the outer cover 18. However, in other embodiments, the bodyside liner 27 and the outer cover 18 may be of the same dimensions in width and length, for example, as depicted in the embodiments illustrated in FIG. 3. In other embodiments, the bodyside liner 27 can be of greater width than the outer cover 18.

It is further contemplated in some embodiments that the bodyside liner 27 may be composed of more than one segment of material such as a central region of material which is different from one or both of lateral regions (not shown) of the bodyside liner 27. The bodyside liner 27 can be of different shapes, including rectangular, hourglass, or any other shape. The bodyside liner 27 can be suitably compliant, soft feeling, and non-irritating to the wearer's skin and can be the same as or less hydrophilic than the absorbent body 26 to permit body exudates to readily penetrate through to the absorbent body 26 and provide a relatively dry surface to the wearer.

The bodyside liner 27 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 27. The bodyside liner 27 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 27 need not be a unitary layer structure, and thus, can include more than one layer of fabrics, films, and/or webs, as well as combinations thereof. For example, the bodyside liner 27 can include a support layer and a projection layer that can be hydroentagled. The projection layer can include hollow projections, such as those disclosed in U.S. Pat. No. 9,474,660 to Kirby et al.

For example, the bodyside 27 can be composed of a meltblown or spunbond web of polyolefin fibers. Alternatively, the bodyside liner 27 can be a bonded-carded web composed of natural and/or synthetic fibers. The bodyside liner 27 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 27 or it can be selectively applied to particular sections of the bodyside liner 27.

In an embodiment, a bodyside liner 27 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 27 can be a spunbond substrate with a basis weight from about 10 or 12 to about 15 or 20 gsm. In an embodiment, a bodyside liner 27 can be a 12 gsm spunbond-meltblown-spunbond substrate having 10% meltblown content applied between the two spunbond layers.

Although the outer cover 18 and bodyside liner 27 can include elastomeric materials, it is contemplated that the outer cover 18 and the bodyside liner 27 can be composed of materials which are generally non-elastomeric. In an embodiment, the bodyside liner 27 can be stretchable, and more suitably elastic. In some embodiments, the bodyside liner 27 can be suitably stretchable and more suitably elastic in at least the lateral direction 4, while in other embodiments the bodyside liner 27 can be stretchable, and more suitably elastic, in both the lateral direction 4 and the longitudinal direction 2.

The front waist panel 12 and the rear waist panel 14 are generally partially elasticated materials which hug a wearer's waist and body when the article 10 is worn. The front waist panel 12 and the rear waist panel 14 may generally comprise a plurality of layers of material with one or more elastic elements, such as elastic elements 21, 23, sandwiched between the layers. FIGS. 9A and 9B depict some embodiments of the front waist panel 12 and the rear waist panel 14 having multiple layers. For instance, the front waist panel 12 can be seen to comprise outer front waist panel layer 82, which has an outer front waist panel surface 91, and inner front waist panel layer 84, which has an inner front waist panel surface 92. Similarly, the rear waist panel 14 may also comprise a plurality of layers. In some embodiments, the layers 82, 84 may be formed from two separate webs, while in other embodiments, the layers 82, 84 may be formed of a single web which has been folded over to form two layers.

In general, the outer front waist panel layer 82 may be formed from any suitable fibrous nonwoven webs. For instance, the outer front waist panel layer 82 may be formed from nonwoven webs such as staple fibers webs and more continuous fiber or filament webs such as are found in meltblown webs and spunbond webs. Through air bonded carded staple fiber webs are particularly suitable for the outer front waist panel layer 82 because such fibers as bicomponent fibers can be used which include polyethylene-based polymers for the sheaths to provide a softer feel and hand, while the cores of the bicomponent fibers can be made from such polymers as polypropylene and polyester (PET) to provide other properties such as rigidity and compression resilience. The inner front waist panel layer 84 can be made from any of the same materials as the outer front waist panel layer 82. In at least some embodiments, the inner front waist panel layer 84 may be made from spunbond webs or combinations of spunbond and meltblown webs which are typically made from polypropylene-based polymers. In general, the basis weight of the front waist panel 12 may be between about 10 gsm and about 100 gsm, including both of the outer front waist panel layer 82 and the inner front waist panel layer 84 and any interpanel adhesive disposed between the inner front waist panel layer 84 and the outer front waist panel layer 82. In other embodiments, the basis weight of the front waist panel 12 may be between about 16 gsm and about 50 gsm, including both of the outer front waist panel layer 82 and the inner front waist panel layer 84 and any interpanel adhesive disposed between the inner front waist panel layer 84 and the outer front waist panel layer 82. In still further embodiments, the basis weight of the front waist panel 12 may be between about 16 gsm and about 35 gsm, including both of the outer front waist panel layer 82 and the inner front waist panel layer 84 and any interpanel adhesive disposed between the inner front waist panel layer 84 and the outer front waist panel layer 82.

Figure 4:
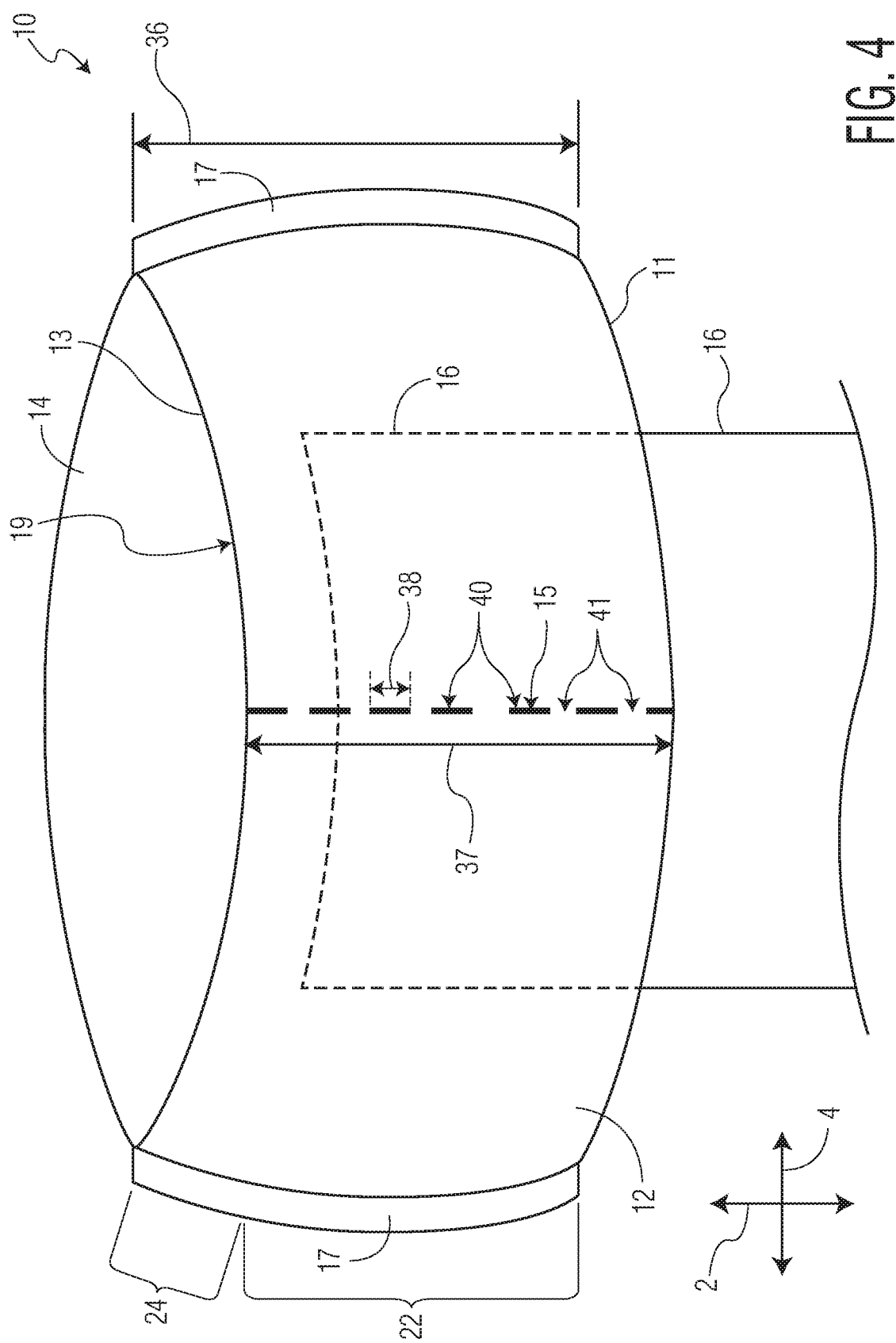
FIG. 4 is a close-up of the front waist panel of the absorbent article of FIG. 1 with the weakened region highlighted.

As seen in FIG. 1, the front waist panel 12 may extend from a front waist panel bottom edge 11 to a front waist panel top edge 13 for a front waist panel length 36 (shown in FIGS. 3 and 4). The front waist panel top edge 13 may correspond to the end of the outer front waist panel layer 82 proximate the elasticated waist band portion 24. As seen better in FIG. 8A, the front waist panel top edge 13 may be disposed at the longitudinal top edge 19 of article 10, however this may not be necessary in all embodiments. In at least some embodiments, such as shown in FIG. 8B, the outer front waist panel layer 82 may include a folded front waist panel portion 90 which is folded over the inner front waist panel layer 84. In such embodiments, the front waist panel top edge 13 may be disposed longitudinally below the longitudinal top edge 19 of article 10.

The absorbent body 26 can be suitably constructed to be generally compressible, conformable, pliable, non-irritating to the wearer's skin and capable of absorbing and retaining liquid body exudates. The absorbent body 26 can be manufactured in a wide variety of sizes and shapes (for example, rectangular, trapezoidal, T-shape, I-shape, hourglass shape, etc.) and from a wide variety of materials. The size and the absorbent capacity of the absorbent body 6 should be compatible with the size of the intended wearer (infants to adults) and the liquid loading imparted by the intended use of the absorbent article 10. The absorbent body 26 can have a length and width that can be less than or equal to the length and width of the absorbent article 10.

In some embodiments, the absorbent body 26 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In at least one embodiment, the absorbent body 26 can be a matrix of cellulosic fluff and superabsorbent material. In various embodiments, the absorbent body 26 may be constructed of a single layer of materials, or in the alternative, may be constructed of two or more layers of materials.

Various types of wettable, hydrophilic fibers can be used in the absorbent body 26. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material or in an alternate embodiment be comprised entirely of superabsorbent material.

Elastic elements 21, 23 may form an elasticated chassis portion 22 and an elasticated waist band portion 24 of the article 10, respectively. Generally, the elastic elements 21, 23 may be disposed between the layers of the front waist panel 12 and the rear waist panel 14 and held in place with an elastic adhesive. Although shown as elastomeric strands in the Figures, the elastic elements 21, 23 may comprise elastic strands, ribbons, or sheets. In some embodiments, the elastic elements 21, 23 may comprise a single unitary elastic element spanning throughout the elasticated chassis portion 22 and the elasticated waist bad portion 24—for example an elastic film. The elastic elements may comprise spandex, natural or synthetic rubber, thermoplastic elastomeric materials, or heat activated elastomeric materials. More generally, the elastic elements 21, 23 can be any elastomeric material capable of being elongated at least about 50 percent, desirably about 350 percent, and capable of recovering to within at least about 250 percent, and desirably about 150 percent of its original length after being elongated about 300 percent. Some specific examples of the elastic elements 21, 23 include where the elastic elements 21, 23 are comprised of a spandex elastomeric strand(s), a thermoplastic elastomer or a natural or a synthetic rubber, or a heat activated elastic material which can be activated with heat treatment after the elastic elements 21, 23 are secured within the front waist panel 12 and the rear waist panel 14.

Figure 6:
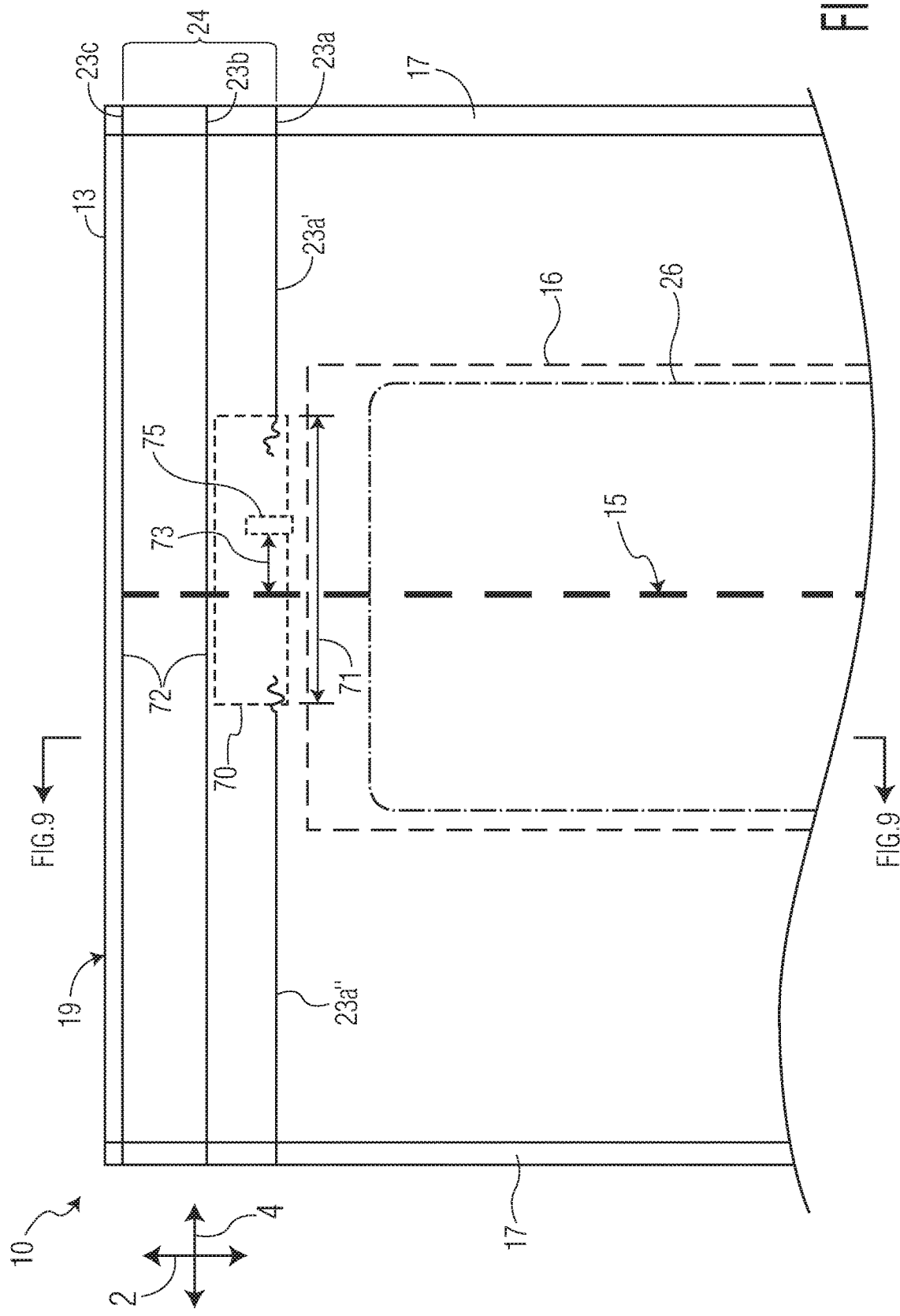
FIG. 6 is a plan view of the front waist panel of the absorbent article of FIG. 1 with elastic elements of the waistband region highlighted.
Figure 7:
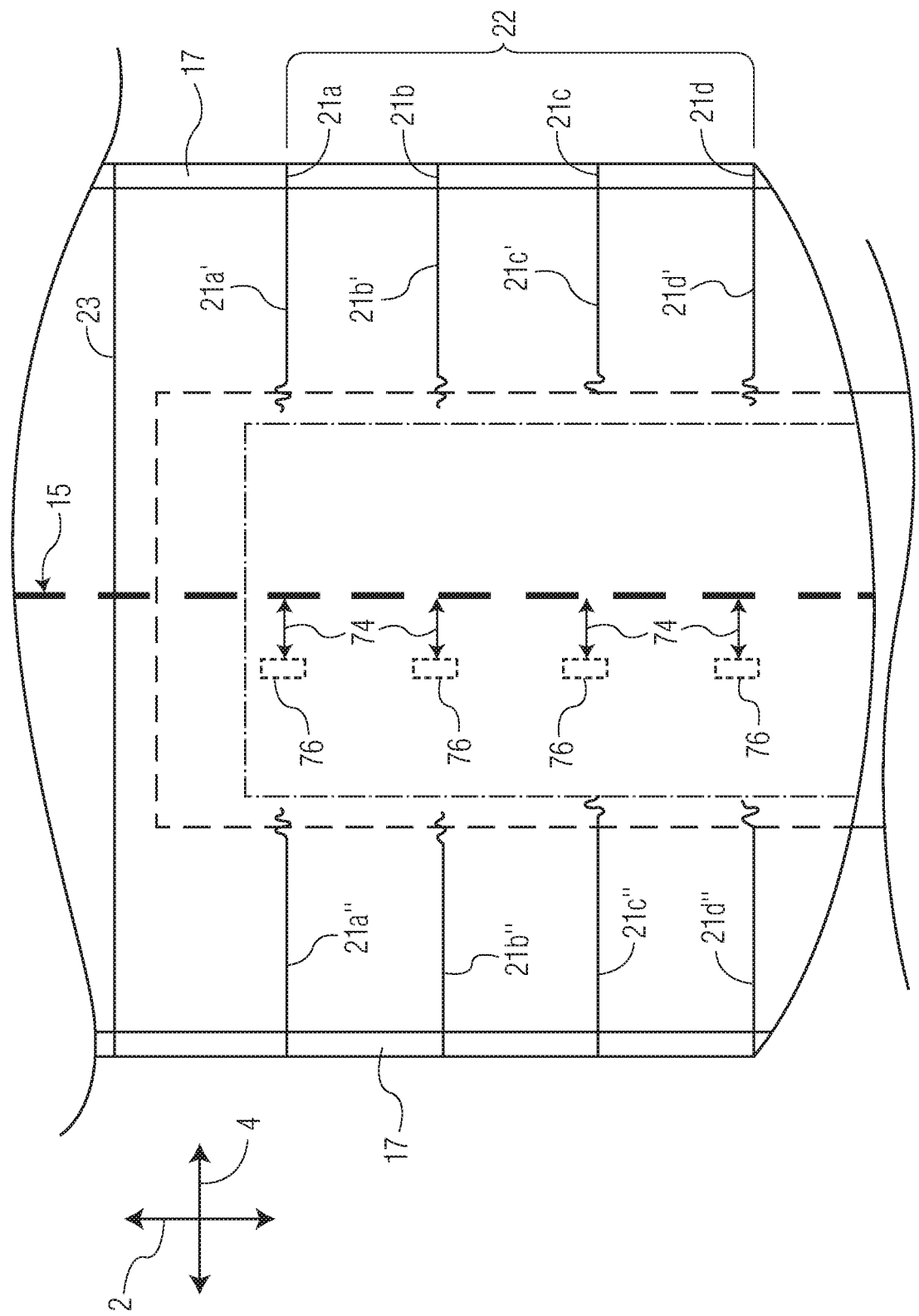
FIG. 7 is a plan view of the front waist panel of the absorbent article of FIG. 1 with elastic elements of the waist portion highlighted.

As seen in more detail in FIGS. 3, 6, and 7, the elastic elements 21, 23 form an elasticated chassis portion 22 and an elasticated waist band portion 24, respectively. The elasticated waist band portion 24 comprises the region of the front waist panel 12 comprising the one or more elastic elements 23 which are disposed closer to the longitudinal top edge 19 of article 10 than the absorbent body 26. In embodiments where the article 10 comprises a plurality of individual elastic elements 23 (such as strands or ribbons or the like), the elasticated waist band portion 24 then comprises the region of the front waist panel 12 which spans from the elastic element 23 longitudinally furthest away from the longitudinal top edge 19 to the elastic element 23 longitudinally closest to the longitudinal top edge 19, where all of the elastic elements 23 are disposed closer to the longitudinal top edge 19 than the absorbent body 26. In embodiments where the elastic element 23 comprises a unitary elastic structure—either separate from, or a part of, elastic elements 21—the elasticated waist band portion 24 may be the region of the front waist panel 12 containing the unitary elastic element 23 that is disposed closer to the longitudinal top edge 19 than the absorbent body 26.

The elasticated chassis portion 22 comprises the region of the panel 12 comprising the one or more elastic elements 21. As shown in the Figures, the elastic elements 21 are the elastic elements for which a portion of the absorbent body 26 is disposed closer to the longitudinal top edge 19 than each of the one or more elastic elements 21. In embodiments where the elastic elements 21 comprise a plurality of individual elastic elements, at least a portion of the absorbent body 26 is disposed closer to the longitudinal top edge 19 of article 10 than each of the elastic elements 21. In embodiments where the elastic elements 21 comprise a unitary elastic element—whether separate from, or a part of, elastic elements 23—the elasticated chassis portion 22 may be the region of the front waist panel 12 containing the unitary elastic element 21 that is disposed further away from the longitudinal top edge 19 of article 10 than at least a portion of the absorbent body 26.

The insert 16, including the absorbent body 26, can overlap at least a portion of the front waist panel 12 and the rear waist panel 14. More particularly, the absorbent body 26 may overlap one or more of the elastic elements 21, as shown in the Figures. In some of these embodiments, as will be described in more detail with respect to FIG. 6, at least one of the one or more elastic elements 21 which overlap the absorbent body 26 may be severed to improve function of the absorbent body 26 and improve fit of the article 10.

As described, the article 10 may be a closed-sided absorbent article. Accordingly, the lateral edges of the article 10 may be closed, such as by side-seam bonds 17. The side-seam bonds 17 are bonds which connect the front waist panel 12 to the rear waist panel 14 on each lateral side of the article 10. These bonds are generally formed through some mechanical means, such as through application of ultrasonic energy, pressure energy, or heat energy, or combinations thereof. Accordingly, the side-seams 17 are generally permanent attachment means between the front waist panel 12 and the rear waist panel 14. However, this is not required in all embodiments of the present disclosure. In other embodiments, the side-seams could be manufactured to be refastenable, or in still further embodiments, the side-seams 17 may be configured to be easily torn to provide another method of removal of the article 10.

Article 10 may further comprise weakened region 15. The weakened region 15 is shown in the figures located on the front waist panel 12. However, in other embodiments, the weakened region 15 could be located on the rear waist panel 14. In still further embodiments, contemplated articles according to the present disclosure may include a weakened region, such as weakened region 15, on both the front waist panel 12 and the rear waist panel 14. Accordingly, it should be understood that the depiction in the figures of the weakened region 15 located only on the front waist panel 12 is for conciseness and ease of description only and is not meant to be limiting in any way. More specifics of the weakened region 15 will be described with respect to FIG. 4, but one of the main functions of the weakened region 15 is to provide a location on the article 10 which is easily torn open by a wearer or caregiver to remove the article 10 from a wearer.

Figure 2:
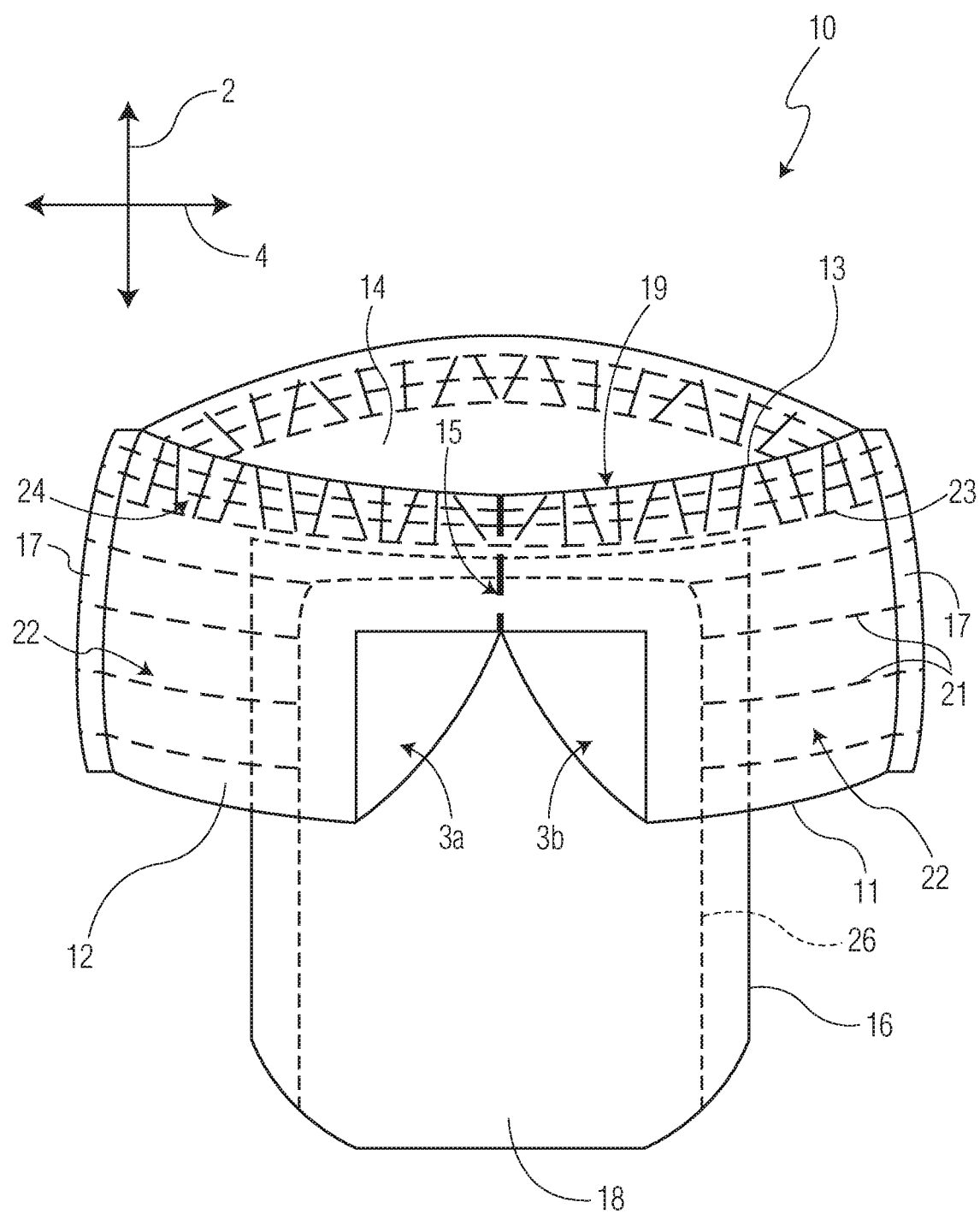
FIG. 2 is a perspective view of the disposable closed-sided absorbent article of FIG. 1, where the front panel is in a partial open position.

FIG. 2 is a perspective view of the disposable closed-sided absorbent article 10 of FIG. 1, where the front panel 12 is in a partial open position. As mentioned, the article 10 may comprise a weakened region 15 which may allow for easy tearing of the front waist panel 12. A wearer or a caregiver may tear open the front waist panel 12 along the weakened region 15 to separate the front waist panel 12 into two separate front waist panel portions. FIG. 2 depicts where the weakened region 15 has been partially torn proximate the front waist panel bottom edge 11 and the two partial-front waist panel portions have been moved toward the front waist panel top edge 13, as indicated by arrows 3a, 3b.

The weakened region 15 may be torn to fully separate the front waist panel 12 into two separate front waist panel portions, as shown in FIG. 3, which is a plan view of the article 10 in the fully open configuration with the front waist panel 12 torn into two separate front waist panel portions 12a, 12b. FIG. 3 depicts further features of the article 10. For example, the body facing surface 25 of the article 10 can be seen, along with containment flaps 28 and leg elastic members 29.

Article 10 may include the containment flaps 28 to help retain bodily exudates within the article 10. Generally, the containment flaps 28 can be of various configurations and shapes, and can be constructed by various methods. For example, the containment flaps 28 may be similar to those containment flaps described in U.S. Pat. No. 5,895,382 to Robert L. Popp et al, U.S. Pat. No. 9,168,181 to Robert L. Popp et al., and U.S. Pat. No. 9,259,362 to Robert L. Popp et al, each of which is incorporated herein by reference in its entirety. The containment flaps 28 can be constructed of a fibrous material which can be similar to the material forming the bodyside liner 27, including, but not limited to a spunbond-meltblown-spunbond ("SMS") material. Other conventional materials, including, but not limited to, polymer films, can also be employed. In addition, laminates of materials including multiple layers of film and/or nonwovens can be used to form the containment flap material.

The containment flaps 28 can include one or more flap elastic members (not shown), such as one member, two members, three members, or any other suitable number of elastic members. The flap elastic members may be located adjacent a flap distal edge, but they can also be located in any other portion of the containment flaps including adjacent a flap proximal portion and a flap medial portion.

The leg elastic members 29 can be secured to the outer cover 18, such as by being bonded thereto by laminate adhesive, generally laterally inward of the longitudinal side edges of the insert 16. The leg elastic members 29 can form elasticized leg cuffs that further help to contain body exudates. In an embodiment, the leg elastic members 29 may be disposed between inner and outer layers (not shown) of the outer cover 18, or between other layers of the absorbent insert 16, for example, between the outer cover 18 and the bodyside liner 27. A wide variety of elastic materials may be used for the leg elastic members 29. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 29 can be formed with the containment flaps 28, and then attached to the chassis insert in some embodiments. Of course, the leg elastic members 29 can be omitted from the absorbent insert 16 without departing from the scope of this disclosure.

FIG. 4 is a close-up of the front waist panel 12 of the article 10 of FIG. 1 with the elastic members 21, 23 and the absorbent body 26 hidden to better highlight the weakened region 15. As described with respect to FIG. 1, the article 10 may include a weakened region 15. In some embodiments, the weakened region 15 may comprise a perforation line while in other embodiments, the weakened region 15 may comprise a mechanically weakened portion of the front waist panel 12. Generally, the weakened region 15 may be formed in the front waist panel 12 through any suitable means. For instance, where the weakened region 15 comprises a perforation line, the front waist panel 12 may be cut or slit in order to form the perforation line. In other embodiments, one or more of the layers of the front waist panel 12 maybe compressed under pressure, thereby weakening the compressed portions relative to the surrounding un-compressed portions. In such embodiments, the front waist panel 12 may be subject to deformation by being fed through a nip, and in particular a nip comprising an anvil roll and a pattern roll where the pattern roll comprises one or more protrusions to compress the front waist panel 12. In still further embodiments, the weakened region 15 may comprise a melted or ablated region of the front waist panel 12. In some embodiments, the weakened region may extend only through one of the layers of material of the front waist panel 12, while in other embodiments the weakened region 15 may extend through all of the layers of the front waist panel 12.

Alternatively, instead of the weakened region 15 being formed in the front waist panel 12, the weakened region 15 may instead be formed during manufacture of one or more pre-cursor webs of material that are used to form the front waist panel 12. For instance, during manufacture of such pre-cursor webs, the pre-curser webs may be formed with weakened regions—whether inherently through the structure of the material itself or through one of the above-identified deformation means. The pre-curser webs may then be used to form the front waist panel 12, and the weakened regions may be registered within the manufacturing process to align each weakened region 15 in relation to an absorbent insert 16 of an individual absorbent article 10.

The weakened region 15 may extend generally between a top end and a bottom end in the longitudinal direction 2 throughout a portion of the front waist panel length 36 and may have a weakened region length 37. The weakened region top end may be the end of the weakened region 15 disposed most proximate the front waist panel top edge 13. The weakened region bottom end may be the end of the weakened region 15 disposed most proximate the front waist panel bottom edge 11. In some embodiments, the weakened region length 37 may be between about 50% and about 100% of the front waist panel length 36. In other embodiments, the weakened region length 37 may be between about 75% and about 100% of the front waist panel length 36. The weakened region 15 may begin at the front waist panel bottom edge 11 and extend longitudinally toward the front waist panel top edge 13. In other embodiments the weakened region 15 may begin at the front waist panel top edge 13 and extend longitudinally toward the front waist panel bottom edge 11.

In at least some embodiments, the weakened region 15 may extend at least partly into the elasticated waist band portion 24, and in further embodiments the weakened region 15 may extend fully through the elasticated waist band portion 24. These embodiments may make it easier for a user or a caregiver to fully tear the front waist panel 12 in order to more easily remove the article 10 but are not required in all embodiments.

Although generally shown as a straight line extending longitudinally through the front waist panel 12, the weakened region 15 may have any suitable orientation and/or shape or pattern. For instance, the weakened region 15 may form an angle between 30 degrees and 90 degrees with respect to the front waist panel bottom edge 11. The weakened region 15 may have a single curve or multiple curves, or may have a stepped or zig-zag pattern. The weakened region 15 could comprise multiple separate shapes or patterns connected together to form a continuous weakened region.

In general, it may be desirable for the weakened region 15 to have a particular tear strength in order for the weakened region 15 to be easily torn open by a wearer or a caregiver. In order to ensure that the weakened region 15 is easily torn, the weakened region 15 may have an average peak shear strength of less than or equal to about 60 N in some embodiments, according to the Average Peak Shear Strength Test Method described herein. In further embodiments, the weakened region 15 may have an average peak shear strength of less than or equal to about 40 N, according to the Average Peak Shear Strength Test Method described herein.

In at least some embodiments, the weakened region 15 may have an average peak shear strength of greater than or equal to about 10 N, 15 N, or 20 N, according to the Average Peak Shear Strength Test Method described herein. These minimum average peak shear strength values may be necessary in order to manufacture the articles 10 in a continuous manufacturing process according the methods described herein. The minimum average shear strength values may allow for the front waist panel 12 to maintain integrity throughout the manufacturing process and to not accidentally tear before being torn by a wearer or caregiver.

In still further embodiments, the weakened region 15 may have a variable average peak shear strength. For example, the weakened region 15 generally comprises a top portion disposed most proximate the front waist panel top edge 13, a bottom portion disposed most proximate the front waist panel bottom edge 11, and a middle portion disposed between these weakened region top and bottom portions.

The weakened region top portion may comprise a length of the weakened region 15 beginning at an end of the weakened region 15 disposed most proximate the front waist panel top edge 13 and extending toward the front waist panel bottom edge 11. The length of the weakened region top portion may be between about 5% and about 25%, or between about 5% about 20%, or between about 5% and about 15% of the weakened region length 37. Likewise, the weakened region bottom portion comprise a length of the weakened region 15 beginning at an end of the weakened region 15 disposed most proximate the front waist panel bottom edge 11 and extending toward the front waist panel top edge 13. The length of the weakened region bottom portion may be between about 5% and about 25%, or between about 5% about 20%, or between about 5% and about 15% of the value of the weakened region length 37.

In use, the weakened region 15 is most likely to be opened by first tearing either the weakened region top or bottom portion. Accordingly, it may be beneficial for the weakened region top portion, bottom portion, or both of the weakened region top portion and bottom portion to have higher average peak shear strengths than the weakened region middle portion. In such embodiments, the weakened region 15 may be less likely to become torn accidently, as the higher average peak shear strength of the weakened region top portion and/or bottom portion helps to prevent accidental tears. However, the weakened region 15 may still be relatively easy for a user to tear completely as the middle portion has a relatively lower average peak shear strength.

In some embodiments, the weakened region top portion may have an average peak shear strength that is between about 10% and about 200%, or between about 25% and about 150%, or between about 25% and about 150%, or between about 25% and about 100%, or between about 25% and about 75% greater than the average peak shear strength of the middle portion. In further embodiments, the weakened region bottom portion may instead have an average peak shear strength that is between about 10% and about 200%, or between about 25% and about 150%, or between about 25% and about 150%, or between about 25% and about 100%, or between about 25% and about 75% greater than the average peak shear strength of the middle portion.

In still further embodiments, both of the weakened region top portion and the weakened region bottom portion may have greater average peak shear strengths than the average peak shear strength of the middle portion. In such embodiments, the weakened region top portion and the weakened region bottom portion may have average peak shear strengths according to any of the ranges listed above relative to the average peak shear strength of the middle portion. It should further be understood that the average peak shear strength of the weakened region top portion and the weakened region bottom portion do not need to be the same. The average peak shear strengths of the different portions of the weakened region 15 can be determined according to the Average Peak Shear Strength Test Method detailed below and using only the application top, middle, or bottom portions of the weakened region 15.

Average Peak Shear Strength Test Method:

The test uses an MTS Criterion 42 machine purchased from MTS, located at 14000 Technology Drive, Eden Prairie, Minn., hereinafter "the machine". The machine is configured with a 10,000-gram load cell and a MTS Model 100/200 Advantage Pneumatic Tensile Grip with a 25×76 mm face grip with interlocking faces. The test then comprises the following steps:

1. Preparation of Apparatus and Materials
   1.1 Verify the appropriate load cell is in the tensile tester.
   Note 1: For load cell conditioning (warm up), refer to the manufacturer's specifications.
   1.2 Install the appropriate grips and grip faces.
   1.3 Ensure the air pressure to operate the grips is set at 90 pounds per square inch (psi).
   1.4 Turn on the computer and then follow the software menu selection.
   1.5 Follow the instructions for calibrating the load cell for the tensile tester being used.
   1.6 Adjust the gauge length.
   1.7 Verify the tensile tester parameters meet the following specifications (see Table 1):

TABLE 1

| | |
|---|---|
| Crosshead Speed | 305 ± 10 mm/minute (12 ± 0.4 inch) |
| Gage Length | 76 ± 1 mm (3 ± 0.04 inch) |

TABLE 1-continued

| | |
|---|---|
| Load Units | Grams-force |
| Full-Scale Load | Use an appropriate load cell for the material being tested so the test value falls between 5 and 95% of the full-scale load. |
| Break Sensitivity | 40% |

1.8 Verify the rolldown travels 100 mm (4 inches) in 2.4±0.5 seconds. Adjust if necessary. Refer to the Speed Adjustments section in the equipment manual.

1.9 Verify the roller stops off the hook fastener after the first cycle; if necessary, adjust the limit switch of the rolldown.

1.10 Ensure the rolldown machine and tensile tester frame are free of fluff and superabsorbent.

Note 3: The rolldown machine should be cleaned (vacuumed free of fluff/superabsorbent) at least once per shift.

2.0 Test Specimen Preparation 2.1 Remove the front panel 12 from the absorbent article. This is done by cutting the front panel 12 along the longitudinal edges of the panel 12 and free-spraying the panel to de-activate the adhesive attaching the front panel 12 to the insert 16.

3.0 Procedure 3.1 Zero the load on the tensile frame.

3.2 Place the specimen in the grips using the following steps:

3.2.1 Place a first side edge of the front panel 12 within the upper grip. The grip should overlap at least 5 mm of the front panel 12. Close the grip.

Note 4: Do not clamp the specimen at an angle; it may affect the test results.

3.2.3 Place a second side edge of the front panel 12 within the lower grip. The grip should overlap at least 5 mm of the front panel 12. Close the lower grip.

3.3 Start the crosshead.

3.4 When the test is finished and the crosshead has returned, remove the specimen from the grips.

4.0 Results

Note 5: The date of testing, and if possible, the date the test product was manufactured should be included with the data.

4.1 For each test specimen, report the maximum load in grams. For each sample set, report the standard deviation, minimum, and maximum values.

4.2 Record the Average Peak Shear Strength in Grams force. Convert the grams force unit into Newtons, and record the Average Peak Shear Strength in Newtons.

In general, the weakened region 15 may comprise individual weakened portions 40 interspersed with non-weakened portions 41. In this manner, the weakened region 15 may comprise a weakened region percentage. This weakened region percentage may be the sum of the length of each of the weakened portions 40, e.g. the addition of each of the weakened portion lengths 38, divided by the overall weakened region length 37. In some embodiments, the weakened region percentage may be between about 45% and about 90%, or between about 65% and about 75%. In other words, the total length of each of the weakened portions 40 comprising the weakened region 15 may comprise between about 45% and about 90% of the weakened region length 37, or between about 65% and about 75% in other embodiments. Weakened region percentages in the ranges described may provide for a weakened region 15 that is sufficiently easy to tear by a user or caregiver by not accidently tear when the article is in use.

In at least some embodiments, the weakened region percentage may differ along different portions of the weakened region 15. For instance, the weakened region 15 may have lower weakened region percentages along the weakened region top and/or bottom portions than along the weakened region middle portion. In different embodiments, the weakened region percentage of the weakened region top portion may be between about 20% and about 70%, or between about 25% and about 60%, or between about 30% and about 50%, while weakened region percentage of the weakened region middle portion is between about 50% and about 95%, or between about 60% and about 90%, or between about 60% and about 80%. In other embodiments, the weakened region percentage of the weakened region bottom portion may be between about 20% and about 70%, or between about 25% and about 60%, or between about 30% and about 50%, while weakened region percentage of the weakened region middle portion is between about 50% and about 95%, or between about 60% and about 90%, or between about 60% and about 80%. In still further embodiments, the weakened region percentage of the weakened region top portion and the weakened region bottom portion may be between about 20% and about 70%, or between about 25% and about 60%, or between about 30% and about 50%, while weakened region percentage of the weakened region middle portion is between about 50% and about 95%, or between about 60% and about 90%, or between about 60% and about 80%. In such embodiments, the weakened region percentage of the weakened region top portion and the bottom portion do not need to be the same. Having differing weakened region percentages may allow for weakened region 15 to have a variable tear strength.

In further embodiments, the weakened portion lengths 38 do not need to all be similar. Instead, the weakened portion lengths 38 of different weakened portions 40 may differ. For example, the weakened portion lengths 38 of the weakened portions 40 in the weakened region bottom portion may be shorter than the weakened portion lengths 38 of the weakened portions 40 in the weakened region middle portion. In another example, the weakened portions 40 in the weakened region top portion may be shorter than the weakened portion lengths 38 of the weakened portions 40 in the weakened region middle portion. Still further, the weakened portion lengths 38 of the weakened portions 40 in the weakened region top portion and the weakened region bottom portion may be shorter than the weakened portion lengths 38 of the weakened portions 40 in the weakened region middle portion and may differ from each other as well.

Figure 5:
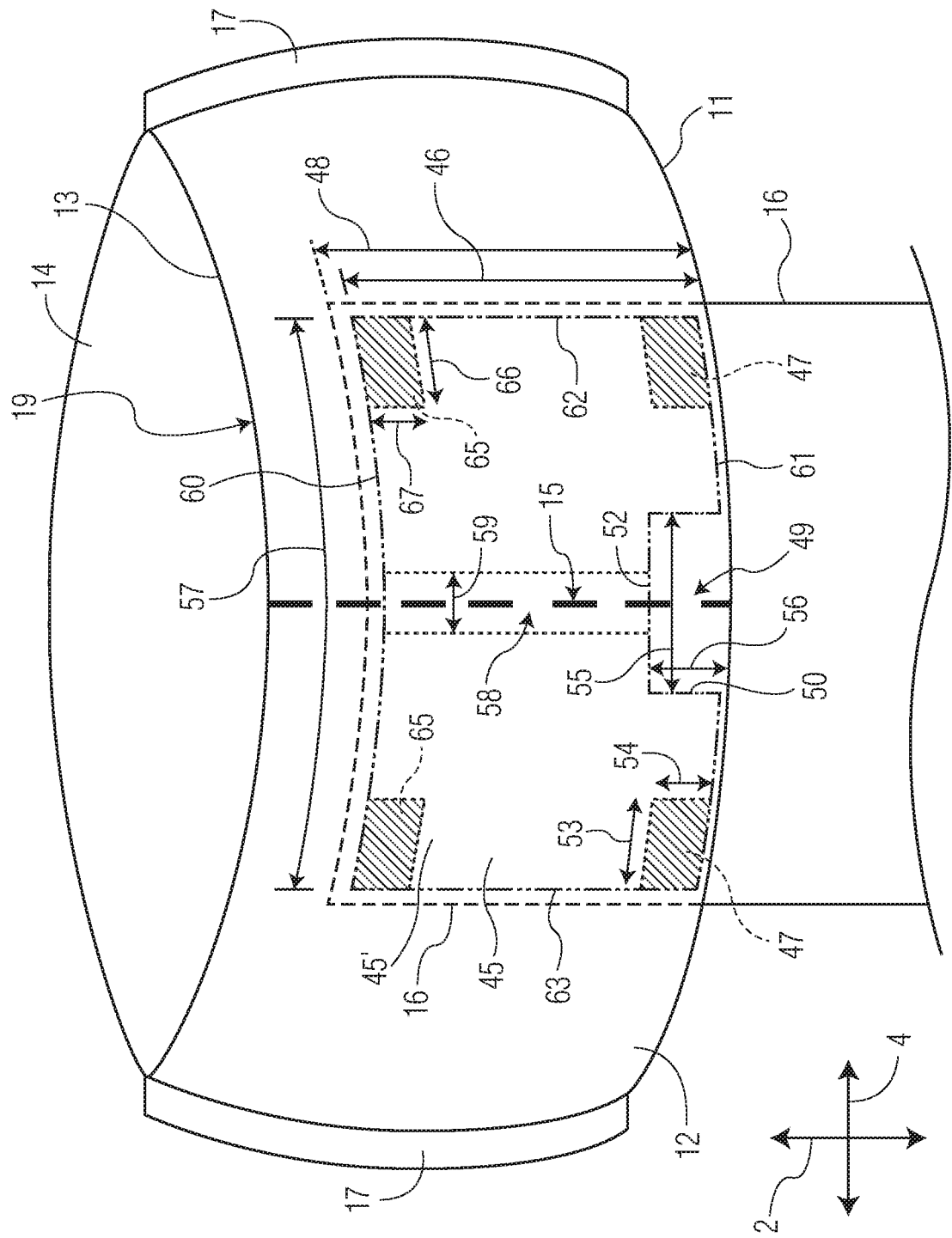
FIG. 5 is a close-up of the front waist panel of the absorbent article of FIG. 1 with the attachment region highlighted.

FIG. 5 is a close-up of the front waist panel 12 of the article 10 with the elastic elements 21, 23 and the absorbent body 26 hidden to highlight the attachment region 45. The attachment region 45 couples the front waist panel 12 to the absorbent insert 16. It should be understood that the attachment region configurations described with respect to FIG. 5 are optional features that, in some embodiments, may be combined with the weakened region 15 in any form described with respect to FIGS. 1-4. That is, some contemplated embodiments of the present disclosure only include the weakened region 15 or only include the described attachment region or regions of FIG. 5, while other contemplated embodiments include both the weakened region 15 and the attachment region or regions of FIG. 5. Accordingly, where present, the attachment region 45 may serve to enhance the function of the article 10 in allowing a user or caregiver to easily open the front waist panel 12 of the article 10, in addition to the other benefits described below with respect to alternative embodiments of the attachment region 45.

In general, the attachment region 45 may have an attachment region top edge 60, an attachment region bottom edge 61, and attachment region longitudinal sides 62 and 63. In some embodiments, the attachment region 45 may span at least a majority of the overlap between the insert 16 and the front waist panel 12. For instance, the attachment region 45 may have an attachment region length 46, while the insert 16 has an insert overlap length 48, which is the length of the absorbent insert 16 which overlaps the front waist panel 12. In some embodiments, the lengths 46 and 48 may be equal, while in other embodiments the length 48 may be somewhat greater than the length 46. Additionally, the attachment region 45 may have an attachment region width 57. Likewise, the width 57 may be the same as the absorbent insert width (not shown), or the absorbent insert width may be somewhat greater than the width 57.

In some optional embodiments, a first adhesive may be disposed throughout the attachment region 45 to couple the insert 16 to the front waist panel 12. In some of these embodiments, this first adhesive may comprise a low-strength adhesive, such as a garment adhesive—sometimes termed a garment attachment adhesive or a garment positioning adhesive in the art. Such a garment adhesive may have a desirable peel strength that is low-enough to allow a user or caregiver to easily peel the front waist panel 12 away from the absorbent insert 16 as the user or caregiver is tearing the weakened region 15. Such desirable peel strengths may be less than about 8 N, 6 N, 4 N, or 2 N, or any other suitable value within the range of about 0.5 N and about 8 N, as measured according to the Angled Peel Test Method described herein.

In other embodiments, the first adhesive may be a higher-strength adhesive such as a construction adhesive or an elastic adhesive—sometimes termed an elastic attachment adhesive in the art. Such higher-strength adhesives may have relatively higher peel performance characteristics than the garment adhesives. For instance, the construction and/or elastic adhesive may have a peel strength of greater than about 8 N, 10 N, or 12 N, or any suitable value above about 8 N, according to the Angled Peel Test Method. Additionally, the construction and/or elastic adhesives may have higher shear strengths than a garment adhesive. The higher shear-strengths able to be achieved by construction and/or elastic adhesive may be beneficial for maintaining the integrity of the attachment between the insert 16 and the front waist panel 12 in use.

In further embodiments the attachment region 45 may comprise two separate adhesives which take advantage of the different benefits of the garment adhesives and the construction/elastic adhesives. For instance, as shown in FIG. 5, the attachment region 45 in some embodiments may comprise a low-strength attachment zone 45' and one or more high-strength attachment zones 47, the one or more high-strength attachment zones 47 each having a high-strength attachment zone width 53 and a high-strength attachment zone length 54. The attachment region 45 may comprise the total area of the front waist panel 12 bounded by both of the attachment zones 45', 47 in these examples. In such embodiments, the low-strength attachment zone 45' may comprise a first adhesive, and the first adhesive may be a garment adhesive having a peel strength according to those preferred peel strengths described above with respect to garment adhesives.

The one or more high-strength attachment zones 47 may comprise a second adhesive which may be a construction or elastic adhesive that has a higher peel strength than the first adhesive. For example, the second adhesive may have a peel strength according to those preferred peel strengths described above with respect to construction/elastic adhesives. Additionally, the second adhesive may also have a shear strength that is higher than the shear strength of the first adhesive. For instance, the second adhesive may have a drop-time of at least about 4 hours according to the Static Shear Test Method described herein. In other embodiments, the second adhesive may have a drop-time of at least about 6 hours, at least about 8 hours, or at least about 10 hours, or any suitable drop-time that is greater than at least about 4 hours, according to the Static Shear Test Method. The first adhesive, on the other hand, may have a drop-time of less than about 4 hours, less than about 2 hours, or less than about 1 hour, or any suitable drop-time that is less than about 4 hours, according to the Static Shear Test Method.

Angled Peel Test Method:

The test uses an MTS Criterion 42 machine purchased from MTS, located at 14000 Technology Drive, Eden Prairie, Minn., hereinafter "the machine". The machine was configured with a 10,000-gram load cell and a MTS Model 100/200 Advantage Pneumatic Tensile Grip with a 25×76 mm face grip with interlocking faces. The test then comprises the following steps:

1.0 Preparation of Apparatus and Materials 1.1 Verify the appropriate load cell is in the tensile tester. For load cell conditioning or warm-up, refer to the manufacturer's specifications.

1.2 Ensure the air pressure to operate the grips is not set beyond the manufacturer's maximum loading specifications.

1.3 Turn on the computer and follow the software menu selection. Follow instructions for calibrating the load cell for the tensile tester being used.

1.4 Ensuring the appropriate grips are installed in the tensile tester such that 305 by 76 mm (12 by 3 inch) grip face is in the top and bottom grip. Ensure the grips and grip faces are free of build-up and the grip faces are free from dents or other damage.

1.5 Adjust the gauge length to 50 mm.

1.6 Verify the tensile tester parameters meet the following specifications. (See Table 2)

TABLE 2

| | |
|---|---|
| Crosshead Speed | 500 ± 10 mm/min |
| Gauge Length | 50 ± 1 mm |
| Load Cell | 100 N load cell |
| Peel Start Calculation | 10 mm |
| Peel End Calculation | 120 mm |
| Test End Point | 130 mm |

2.0 Test Specimen Preparation 2.1 Open up the side panels at the side seam bonds and spread the article flat. Mark the front right and back left of the product as worn.

2.2 Cut the article in half approximately 51 mm (2 inches) below the panel elastic in the front and back of the product. Do not cut the waist elastic.

3.0 Procedure 3.1 Place the absorbent pad in the bottom grip parallel to the waist elastic.

3.2 Place the elastic panel at the leg area in the upper grip so the start of the adhesive attachment is aligned with the center of the grip.

3.3 Ensure the load is between 10-15 grams-force.

3.4 Start the crosshead 3.5 When the test is finished and the crosshead has returned, remove the specimen from the grip.

4.0 Results 4.1 Report the average load to the nearest 0.01 grams-force.

4.2 Convert the reported grams-force to Newtons and record the Newtons value.

Static Shear Test Method:

The Static Shear Test Method uses a commercially available oven with set-point control, a 2-inch hook, and a 1000-gram weight. The Static Shear Test Method also uses an oven rack to which specimens may be attached while disposed within the oven.

1.0 Preparation of Apparatus and Materials 1.1 Verify the oven temperature is 37.8±2° C. (100±3.6° F.).

2.0 Test Specimen Preparation 2.1 Remove an absorbent article from packaging.

2.2 Cut a sample specimen from the absorbent article comprising the front waist panel and the insert where the insert is bonded to the front waist panel through either the low-strength attachment zone or one of the high-strength attachment zones (depending on which adhesive is being tested). The sample specimen should be approximately 51 mm by 51 mm with at least 10 mm ends on each side comprising only the front waist panel or the insert.

3.0 Procedure 3.1 Attach one of the edges of the sample specimen comprising only the front waist panel or the insert to the oven rack using a bulldog clip.

3.2 Attach the weight bar to the other one of the edge of the sample specimen comprising only the front waist panel or the insert, such as by folding the edge over the weight bar and stapling it to itself.

3.3 Place the test rack in the oven. Ensure that all specimens are still attached properly.

3.4 Attach a 1000-gram weight to each weight bar. The weight should hang freely with a minimum of 38 mm (1.5 inches) between the bottom of the weight bar and the bottom of the testing rack; the weight should be high enough above the testing base that the weight falls rather than allowing the material to stretch.

3.6 After each hour, check the specimens for failures. Note on the data sheet which specimens failed.

3.7 This test is run for a total of 8 hours.

3.8 Failure is defined when the weight has dropped.

3.9 Remove the weights and the testing rack from the oven when the test is complete.

4.0 Results 4.1 Report each specimen as a pass or fail at each check.

4.1.1 Pass—When the weight is still hanging.

4.1.2 Failure—Occurs when the weight has dropped. Indicate the hour the failure occurred.

The one or more high-strength attachment zones 47 may be positioned in different locations relative to the front waist panel 12 in different embodiments. For instance, in some embodiments the one or more high-strength attachment zones 47 may be disposed proximate a longitudinal side 62 and/or 63 of the attachment region 45. In further embodiments, the one or more high-strength attachment zones 47 may be additionally or alternatively disposed proximate the attachment region bottom edge 61.

In some embodiments, the one or more high-strength attachment zones 47 may be disposed within the attachment region 45 such that the one or more high-strength attachment zones 47 at least partially overlap the low-strength attachment zone 45'. In further embodiments, the one or more high-strength attachment zones 47 may completely overlap the low-strength attachment zone 45'. In yet other embodiments, the one or more high-strength attachment zones 47 may be disposed entirely outside of the low-strength attachment zone 45' such that there is no overlap between the zone(s) 47 and 45'. Instead, the one or more high-strength attachment zones 47 may be disposed proximate the low-strength attachment zone 45' such that the one or more high-strength attachment zones 47 and low-strength attachment zone 45' may share portions of one or more boundaries of the zones 45', 47.

In some embodiments, the high-strength attachment zone width 53 may be between be at least about 5 mm, or at least about 7.5 mm, or at least about 10 mm, or at least about 12.5 mm, or at least about 15 mm, or at least about 20 mm, and may be less than about 100 mm, or less than about 80 mm, or less than about 60 mm, or less than about 40 mm. In other embodiments, the high-strength attachment zone width 53 may be between about 5% and about 50%, or between about 15% and about 50%, or between about 25% and about 50% of the attachment region width 57. In other embodiments, the high-strength attachment zones 47 may have high-strength attachment zone widths 53 such that the zones 47 extend all the way between the attachment region longitudinal sides 62, 63 and the recess side edges 50, 51 (described in more detail below). In such embodiments, the high-strength attachment zones 47 may not overlap the low-strength attachment zone 45'.

The high-strength attachment zone length 54 may be between be at least about 2.5 mm, or at least about 5 mm, or at least about 7.5 mm, or at least about 10 mm, and may be less than about 200 mm, or less than about 175 mm, or less than about 150 mm, or less than about 125 mm, or less than about 100 mm, or less than about 75 mm, or less than about 50 mm, or less than about 40 mm, or less than about 30 mm, or less than about 20 mm. In further embodiments, the high-strength attachment zone length 54 may extend all the way from the attachment region bottom edge 61 to the attachment region top edge 60. In these embodiments, the high-strength attachment zones 47 may not overlap the low-strength attachment zone 45'.

The one or more high-strength attachment zones 47 may additionally have relatively small areas as compared to the area of the low-strength attachment region zone 45'. Each of the one or more high-strength attachment zones 47 may comprise an area between about 0.5% and about 10% of the area of the low-strength attachment zone 45'. The relatively small areas of one or more high-strength attachment zones 47 may allow for a relatively large portion of the front waist panel 12 to be peeled from the absorbent insert 16 relatively easily, only leaving relatively small portions of the front waist panel 12, e.g. the one or more high-strength attachment zones 47, which may be more difficult to peel from the insert 16. Yet, the one or more high-strength attachment zones 47 having a higher relative shear strength than the low-strength attachment zone 45' may still allow for the attachment between the front waist panel 12 and the insert 16 to maintain its integrity while the product is in use.

In some additional or alternative embodiments, the article 10 may further include secondary high-strength attachment zones 65. Such secondary high-strength attachment zones 65 may be similar to the high-strength attachment zones 47, except that the secondary high-strength attachment zones 65 may be positioned in different locations than the high-strength attachment zones 47. For example, the secondary high-strength attachment zones 65 may have similar properties to those described with respect to the high-strength attachment zones 47. In particular, the secondary high-strength attachment zones 65 may have peel strengths and/or shear strengths within those ranges described with respect to the high-strength attachment zones 47. These properties may be achieved by using the same adhesives for each of the zones 47, 63, but this does not need to be the case in all embodiments. The zones 47, 63 may comprise different adhesives or one of the zones 47, 63 may comprise an adhesive and the other of the zones 47, 63 may comprise one or more mechanical bonds.

The secondary high-strength attachment zones 65 may be positioned proximate the attachment region top edge 60, and also proximate the attachment region longitudinal sides 62 and 63 in further embodiments. Each of the secondary high-strength attachment zones 65 may have secondary high-strength zone widths 66 and secondary high-strength zone lengths 67. In some embodiments, the widths 66 and lengths 67 may mirror the widths and lengths 53 and 54. In other embodiments, the width 66 and lengths 67 may be larger or smaller than the widths 53 and/or lengths 54. While shown as confined to upper side regions of the attachment region 45 in FIG. 5, in at least some embodiments, the secondary high-strength attachment zones 65 may have widths 66 which are between about 5% and about 50%, or between about 15% and about 50%, or between about 25% and about 50% of the attachment region width 57. In embodiments where the widths 66 are about 50% of the attachment region width 57, there may only be one secondary high-strength attachment zone 65 that extends fully between the attachment region longitudinal sides 62 and 63. Further, like the high-strength attachment zones 47, in some embodiments the secondary high-strength attachment zones 65 may at least partially overlap the low-strength attachment zone 45' in some embodiments while not overlapping the low-strength attachment zone 45' in other embodiments.

In some embodiments, the first adhesive and the second adhesive, e.g. the adhesives which form the low-strength attachment zone 45' and the high-strength attachment zone (s) 47 (and possibly zone(s) 65), respectively, may be applied through the same adhesive head. In such embodiments, the first adhesive and the second adhesive need to have similar operating, or application, temperatures. In this context, the term 'similar' means operating, or application, temperatures within 5 degrees C. of one another. Of course, in embodiments where separate adhesive heads are used to apply the first adhesive and the second adhesive, the operating, or application, temperatures of the first adhesive and the second adhesive do not need to be similar.

Although not required, in any of the above described embodiments, the first adhesive may be a pressure sensitive adhesive. In such embodiments, the first adhesive may have a refastenable property where the front waist panel 12 may be able to be re-applied to the absorbent insert 16 after separation and maintain the re-attachment with the insert 16. Such embodiments may allow for a compact disposal configuration of the article 10, where the absorbent insert 16 is folded or rolled up after the front waist panel 12 has been separated from the insert 16, and then the front waist panel portions 12a, 12b are re-attached to the insert 16 to maintain the insert 16 in the folded or rolled state.

In further embodiments, instead of the one or more high-strength attachment zones 47 comprising the second adhesive, the one or more high-strength attachment zones 47 may comprise one or more mechanical bonds. For instance, the one or more high-strength attachment zones 47 may comprise a plurality of bonds which give the one or more high-strength attachment zones 47 the above described shear strength properties. The one or more high-strength attachment zones 47 may also have a peel strength low enough for the bonds to be broken by a user or a caregiver opening up the front waist panel 12. In other embodiments, however, the bonds may be strong enough that the material of the front waist panel 12 rips around the bonds, instead of the bonds breaking, in order to separate the front waist panel 12 from the insert 16. The bonds may be formed with ultrasonic, pressure, or heat energy, or a combination thereof.

In some additional embodiments, the attachment region 45 may further comprise a recess 49. Where the attachment region 45 comprises a low-strength attachment zone 45' and one or more high-strength attachment zones 47, the recess 49 may be formed as a recess in the low-strength attachment zone 45'. As shown in FIG. 5, the recess 49 may comprise a first recess side edge 50, a second recess side edge 51, and a recessed edge 52. The recess 49 may further have a recess width 55 and a recess length 56. The recess width 55 may be defined as the largest distance between the first recess side edge 50 and the second recess side edge 51. The recess length 56 may be defined as the largest distance between the recessed edge 52 and the front panel bottom edge 11.

In general, the recess 49 defines a region where there is no attachment between the front waist panel 12 and the absorbent insert 16. Although shown as rectangular, the recess 49 may have any suitable shape. For instance, the first recess side edge 50 and the second recess side edge 51 may be angled so that the recess 49 has a triangular or trapezoidal shape. Alternatively, the first recess side edge 50 and the second recess side edge 51 may be curved so that the recess has a semi-circular, or semi-ovular shape.

The recess 49 may be sized to receive one or more fingers of a user or caregiver in order to provide a location for easy starting of tearing the weakened region 15. Accordingly, in some embodiments, the recess width 55 may be about 10 mm, 15 mm, 20 mm, or 25 mm, or any value within the range of about 10 mm to about 25 mm. In other embodiments, the recess width 55 may be about 30 mm, 35 mm, 40 mm, 45 mm, 50 mm, 55 mm, 60 mm, or any suitable value within the range of about 30 mm to about 60 mm, for example to allow space for multiple fingers.

In some embodiments, the recess 49 may be relatively centered within the front waist panel 12. In such embodiments, a portion of the first recess side edge 50 closest to the attachment region longitudinal side edge 63 may be located a distance away from the longitudinal side edge 63 between about 15% and about 40% of the attachment region width 57. A portion of the second recess side edge 51 closest to the attachment region longitudinal side edge 62 may additionally, or alternatively, be located a distance away from the longitudinal side edge 62 between about 15% and about 40% of the attachment region width 57.

In some still further embodiments, the attachment zone 45 may comprise another feature, in combination with any of the above described features of the attachment zone 45 such as high-strength attachment zones 47, the secondary high strength attachment zones 65, and the recess 49—the attachment zone 45 may include an adhesive-less region disposed around the weakened region 15 which is devoid of adhesive (either the first adhesive and/or the second adhesive). For instance, the embodiment of FIG. 5 depicts adhesive-less region 58. Further, where the articles 10 comprises a weakened region 15, the weakened region 15 may extend through adhesive-less region 58. The lack of adhesive within the adhesive-less region 58, and thus a lack of attachment between the front waist panel 12 and the absorbent insert 16, may enhance the ability of a wearer or caregiver to tear the front waist panel 12 along the weakened region 15. For instance, where the attachment region 45 comprises the adhesive-less region 58, breaking the weakened region 15 may occur in a more smooth, controlled manner than in embodiments where the attachment region 45 does not comprise the adhesive-less region 58. The adhesive-less region 58 may have an adhesive-less region width 59 which may generally range from between about 4 mm to about 26 mm, or between about 8 mm and about 22 mm, or between about 12 mm and about 18 mm. These ranges for the adhesive-less region width 59 may generally allow for positioning of the weakened region 15 within the adhesive-less region 58 during manufacture of the article 10, while not being so great as to impair the function or performance of the article 10. The weakened region 15 may generally extend through a middle region of the adhesive-less region 58, but it is not necessary that the weakened region 15 be positioned exactly at the center of the adhesive-less region 58 adhesive-less region 58.

FIG. 6 depicts a plan view of the front waist panel 12 of the article 10, with an outer layer of the front waist panel 12 removed and the one or more elastic elements 21 of the elasticated chassis portion 22 hidden to highlight features of the one or more elastic elements 23a, 23b, 23c. More particularly, FIG. 6 depicts a close-up of the elasticated waist band portion 24 of the article 10. Again, although shown as elastomeric strands, the one or more elastic elements 23a, 23b, 23c could be ribbons, or even a single unitary elastic member.

In some additional, or alternative, embodiments, it may be beneficial for the elasticated waist band portion 24 to include at least one non-elasticized region, such as region 70. The non-elasticized region 70 may be disposed laterally between elasticized regions. For example, as can be seen in FIG. 6, the non-elasticized region 70 extends generally between elastic members 23a', 23a" in the lateral direction 4 which may form elasticized regions within the panel 13.

More generally, the non-elasticized region 70, and other non-elasticized regions, may be formed where a first one of the elastic elements 23, such as elastic element 23a' of FIG. 6, is spaced laterally from a second one of the elastic elements 23, such as elastic element 23a" of FIG. 6. The lateral space between the elastic elements 23a', 23a", e.g. the non-elasticized region lateral length 71, and any longitudinal space between longitudinally adjacent elastic elements 23, such as elastic element 23b in FIG. 6, comprises the non-elasticized region 70, e.g. a region where no elastic elements are present. It may be desirable to have elastic elements in the waistband portion 24 extend continuously throughout the waistband portion to help the article 10 maintain a good fit with a wearer. Accordingly, in order to minimize an effect on the fit of the article 10, the non-elasticized region lateral length 71 may be relatively small, such as between about 2 mm and about 20 mm, or between about 2 mm and about 10 mm.

The elements 23a', 23a" may be formed with space therebetween during manufacture of the article 10. In other embodiments, one of the one or more elastic elements 23, such as element 23a in FIG. 6, may be severed to create two separate elastic elements, 23a', 23a". In these embodiments, the non-elasticized region 70 may then form as the elastic elements 23a', 23a" retract away from each other.

In the example of FIG. 6, the non-elasticized region 70 is shown as only extending through a portion of the elasticated waistband portion 24. For example, only one of the elastic elements 23a, 23b, 23c of the elasticated waistband portion

24 is comprised of two parts, 23a', 23a", with space therebetween. However, in other optional embodiments, additional of the elastic elements 23a, 23b, 23c may be formed in separate portions spaced from each other, or severed to create two separate portions with space forming therebetween through retraction of the two separate portions. In some particular embodiments, all of the elastic elements 23a, 23b, 23c of the elasticated waist band portion 24 may be formed in separate portions spaced from each other or severed to create two separate portions with space forming therebetween through retraction of the separate portions. In such embodiments, the non-elasticized region 70 may span longitudinally between each of the elastic element portions 23a, 23b, 23c, and possibly through the entire elasticated waist band portion 24.

Additionally, as can be seen, the weakened region 15 may extend through the non-elasticized region 70. In such embodiments, a user or caregiver may have an easier time opening the front waist panel 12 than embodiments without an non-elasticized region 70. For example, the user or caregiver would not need to tear through one or more of the elastic elements 23a, 23b, 23c where the weakened region 15 extends through the elasticated waistband portion 24.

Where the non-elasticized region 70 is formed through severing one or more of the elastic elements 23a, 23b, 23c of the elasticated waistband portion 24, an important parameter is where the severing occurs in relation to the weakened region 15. In the embodiment of FIG. 6 where the non-elasticized region 70 extends through only part of the elasticated waistband portion 24, dotted box 75 represents a location where the elastic element 23 may be severed and is located a cutting distance 73 away from the weakened region 15. The cutting distance 73 may be between about 1 mm and about 10 mm, or between about 1 mm and about 5 mm. Severing the elastic element 23a is generally undesirable as it severs the integrity of the elasticated waist band portion 24 of the article 10 which can impair a desired fit of the article 10. Accordingly, to minimize affecting the fit of the article 10, the cutting distance 73 should be relatively close to the weakened region 15 in order to minimize the extent of the non-elasticized region 70 in the lateral direction 4 within the elasticated waist band portion 24.

In some embodiments, severing of the elastic element 23 may be done through use of a knife roll/anvil roll pair. For instance, the dotted box 75 may represent a protrusion of the knife roll of the knife/anvil roll pair. In some embodiments, the protrusion of the knife roll may sever the elastic element 23a without severing either of the layers of the front waist panel 12. However, in other embodiments, the elastic element 23a may be severed through other methods known in the art. Additionally, it should be further understood that although the un-elasticized region 70 is shown as only spanning between one of the elastic elements 23a, 23b, 23c in the embodiment of FIG. 6, the non-elasticized region 70 may span through additional of the elastic elements of the elasticated waistband portion 24 in other embodiments. In these embodiments, one or more of the other elastic elements 23b, 23c of the elasticated waistband portion 24 may be severed in a similar manner.

As described above, the one or more elastic elements 21, 23 of the article 10 may be held in place by coating the elastic elements 21, 23 in elastic adhesive before or during incorporation of the elastic elements 21, 23 into the article 10. Where one or more of the elastic elements 23a, 23b, 23c of the elasticated waistband portion 24 are severed, the elastic adhesive applied to the elastic elements 23a, 23b, 23c which will be severed may be pulsed on and off. More particularly, the elastic adhesive may be pulsed off in a zone around the weakened region 15. In the example of FIG. 6, prior to severing, the elastic element 23a may have an region which is uncoated by any elastic adhesive. In the process of forming the non-elasticized region 70, this uncoated region is registered to overlap with the weakened region 15. The uncoated region may have a lateral extent approximately equal to the un-elasticized region lateral length 71, which may range between about 2 mm and about 20 mm. When the elastic element 23a is severed, the portions 23a' and 23a" retract away from each other to approximately the edges of the uncoated region of the elastic element 23a, which corresponds to the edges of the non-elasticized region 70.

In other embodiments, however, the elastic adhesive may not be pulsed on and off. In such embodiments, the one or more of the elastic elements 23 may still be severed, but there may be little to no retraction of the two portions of the severed elastic elements 23 away from each other. Such embodiments still provide an advantage of an easier to open front waist panel 12, as the user or caregiver will still not need to tear through the one or more elastic elements 23.

FIG. 7 depicts a plan view of the front waist panel 12 of the article 10, with an outer layer of the front waist panel 12 removed to highlight features of the one or more elastic elements 21a, 21b, 21c, 21d. More particularly, FIG. 7 depicts a close-up of the elasticated chassis portion 22 of the article 10. Again, although shown as elastomeric strands, the one or more elastic elements 21a, 21b, 21c, 21d could be ribbons, or even a single unitary elastic member.

In some additional, or alternative, embodiments, it may be beneficial for the elasticated chassis portion 22 to include an un-elasticized region which generally spans the absorbent body 26 of the article 10. Providing an un-elasticized region over the absorbent body 26 may help with the performance of the absorbent body 26 and/or may enhance appearance of graphics located over the absorbent body. Providing the un-elasticized region over the absorbent body 26 will also help to make opening of the front waist panel 12 easier for a user or a caregiver. For example, opening the front waist panel 12 may then not require tearing through one or more elastic elements of the front waist panel 12.

In general, any un-elasticized region located within the elasticated chassis portion 22 may be formed similarly to the un-elasticized region 70 described above with respect to the elasticated waistband portion 24. For example, where the elasticated chassis portion 22 comprises such an un-elasticized region, this un-elasticized region may be formed by severing one or more of the elastic elements 21a, 21b, 21c, 21d forming two elastic element portions which retract away from each other to form the un-elasticized region. In these embodiments, dotted-line boxes 76 may represent locations where the one or more of the elastic elements 21a, 21b, 21c, 21d may be severed. As can be seen, the boxes 76 are located a cutting distance 74 away from an edge of the weakened region 15. The cutting distance 74 may have similar values to cutting distance 73. Although in some embodiments, the cutting distance 74 may be greater than the cutting distance 73.

Additionally, as with the elastic elements 23 of the elasticated waistband portion 24, in some embodiments elastic adhesive applied to the elastic elements 21a, 21b, 21c, 21d may be applied in a pulsed fashion. For instance, the elastic adhesive may be applied to the elastic elements 21a, 21b, 21c, 21d in an intermittent fashion, and the regions of the elastic elements 21a, 21b, 21c, 21d which do not contain the elastic adhesive may be registered during manufacturing to align approximately with the absorbent body 26.

When the elastic elements 21a, 21b, 21c, 21d are severed, the elastic element portions may retract away from each other and leaving a region covering at least a portion of the absorbent body 26 devoid of any elastic elements. Within the chassis region 22, it is less important to control the cutting distance 74 as tightly around the weakened region 15 due to the relatively large desired un-elasticized region covering a majority of the absorbent body. Accordingly, the cutting distance 74 may be between about 1 mm and about half of a width of the absorbent body 26. Although, in other embodiments the elastic adhesive may not be pulsed during application to the elastic elements 21a, 21b, 21c, 21d. In such embodiments, the cutting distance 74 may be between about 1 mm and about 10 mm, or between about 1 mm and about 5 mm.

Figure 8A:
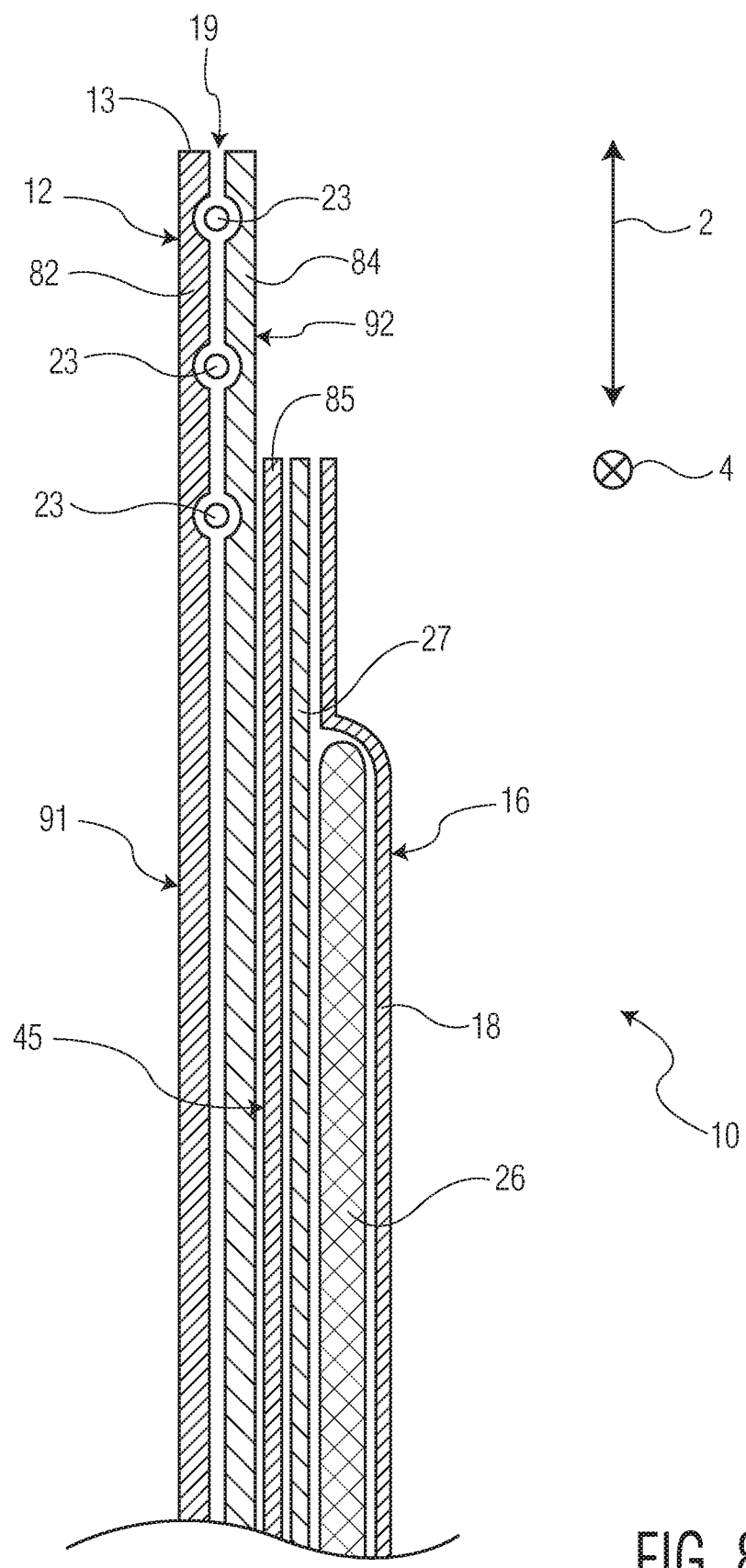
FIG. 8A is a cross-section of the absorbent article shown in FIG. 6 as viewed along line 9-9.
Figure 8B:
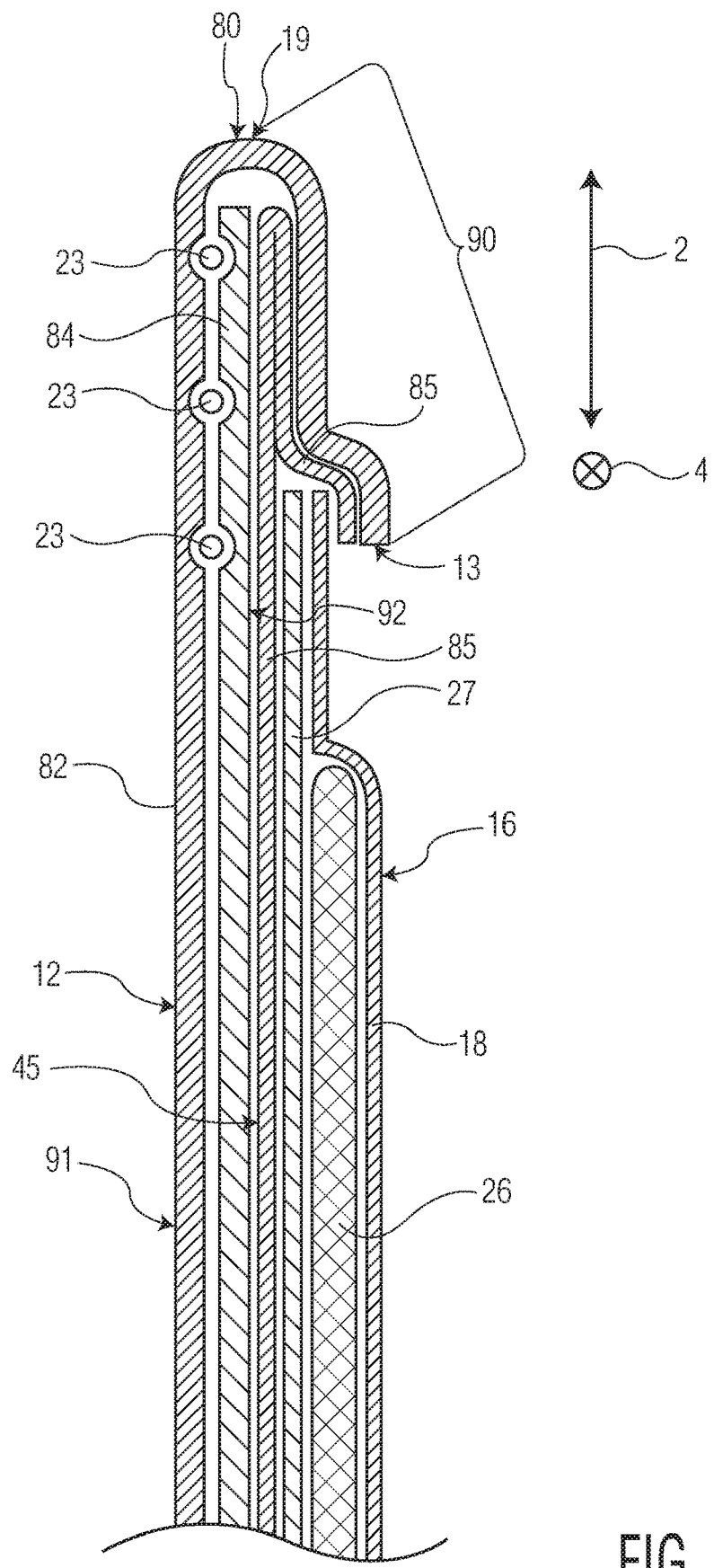
FIG. 8B is a cross-section of an alternative embodiment of the absorbent article shown in FIG. 6 as viewed along line 9-9.

FIGS. 8A and 8B provide alternative embodiments of article 10, and more specifically the front waist panel 12 of article 10. In the embodiment of FIG. 8A, which is a cross-section of the article 10 shown in FIG. 6 as viewed along line 9-9, the front waist panel 12 extends longitudinally above the insert 16, and the longitudinal top edge 19 of the article 10 coincides with the front waist panel top edge 13. Adhesive 85 can be seen attaching the front waist panel 12 to the insert 16. Accordingly, the adhesive 85 can comprise one of the first adhesives described previously with respect to the attachment region 45 shown in FIG. 4.

FIG. 8B shows an alternative embodiment of a cross-section of the article 10 of FIG. 6 as viewed along line 9-9. In the embodiment of FIG. 8B, the front waist panel 12 can include a fold 80 and a folded front waist panel portion 90. In such embodiments, the outer front waist panel layer 82 can be folded over the inner front waist panel layer 84 such that a portion of the outer front waist panel layer 82 is disposed proximate the inner front waist panel surface 92. In some embodiments, the outer front waist panel layer 82 may cover at least a portion of the insert 16, as shown in FIG. 8B. Although, it should be understood that this is not necessary in all embodiments. The outer front waist panel layer 82 may be secured to the inner front waist panel surface 92, and possibly the insert 16 in some embodiments, with adhesive 85. In at least some embodiments, the adhesive 85 may be the same as the first adhesive described previously with respect to FIG. 4.

Figure 9:
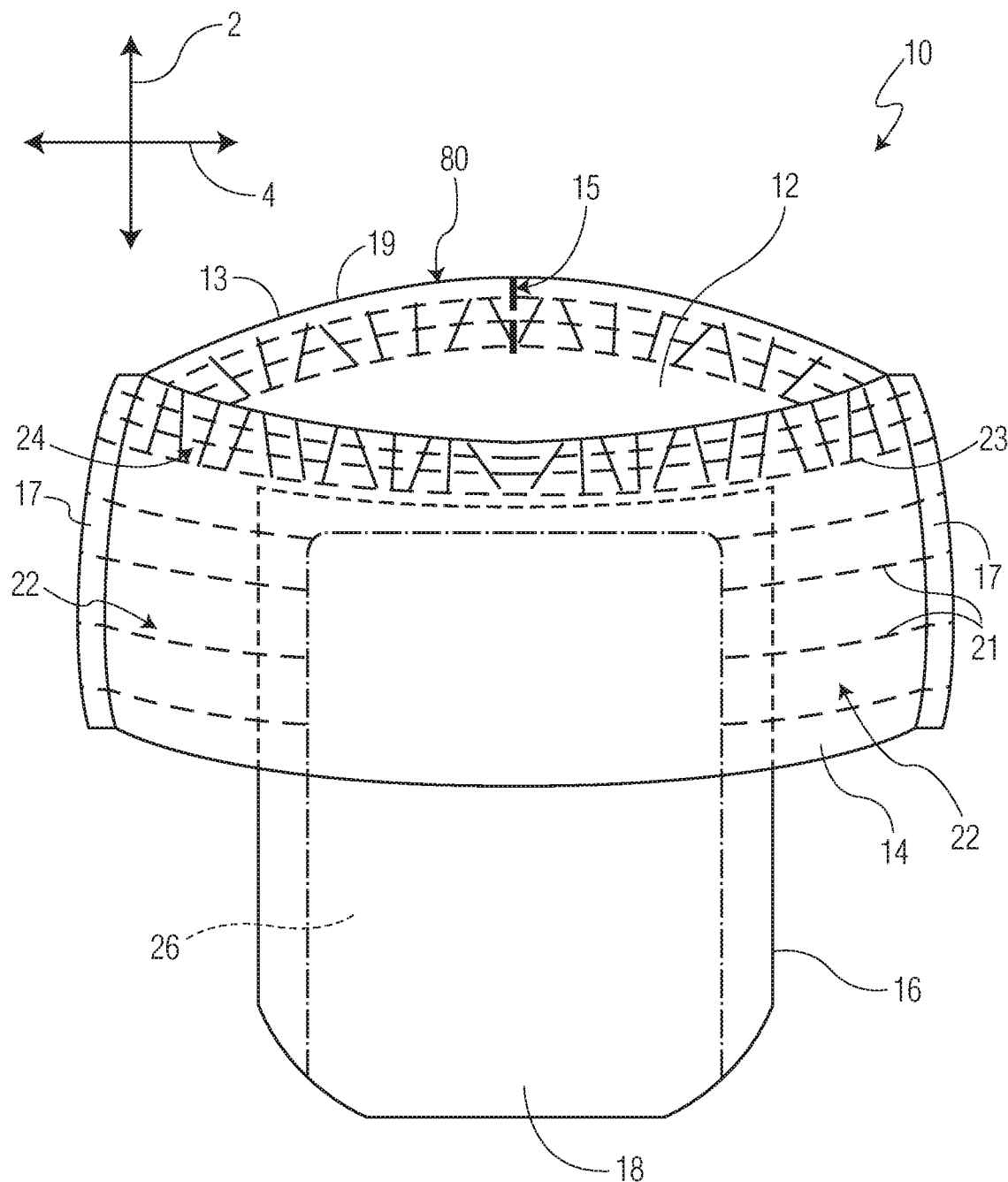
FIG. 9 is a perspective view of the absorbent article of FIG. 1 shown from an opposing view of that in FIG. 1.

In embodiments such as FIG. 8B, the longitudinal top edge 19 of article 10 may not coincide with the front panel top waist edge 13. Rather, the front panel top waist edge 13 may be disposed longitudinally below the longitudinal top edge 19 of article 10, as shown in FIG. 8B. In embodiments where the article 10 includes the fold 80, the weakened region 15 may extend through the fold 80 and into at least part of the folded front waist panel portion 90, as can be seen in FIG. 9, which is a perspective view of article 10 shown from an opposing view of that in FIG. 1. In these embodiments, the weakened region top edge may be disposed in the folded front waist panel portion 90. In at least some embodiments, the weakened region 15 may extend wholly through the folded front waist panel portion 90 to the front waist panel top edge 13. Such embodiments may make for easier opening of the front waist panel 12 by a user or a caregiver.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

What is claimed is:

1. An absorbent article including front region, a crotch region, and a rear region, the article having a first side edge and a second side edge and further comprising:
    an absorbent insert comprising an outer cover, a liner, and an absorbent core disposed between the outer cover and the liner;
    a first waist panel coupled to the absorbent insert throughout a first attachment region; and
    a second waist panel coupled to the absorbent insert throughout a second attachment region, the second waist panel being coupled to the first waist panel proximate the first side edge of the absorbent article and the second side edge of the absorbent article and further comprising a weakened region,
    wherein the second attachment region comprises an attachment region top edge, an attachment region bottom edge, attachment region longitudinal side edges, and an overall attachment region area,
    wherein the second attachment region further comprises a low-strength attachment zone and a high-strength attachment zone, the high-strength attachment zone being disposed proximate the attachment region bottom edge, and
    wherein the low-strength attachment zone has a first peel strength and the high-strength attachment zone has a second peel strength, the second peel strength being greater than the first peel strength.

2. The absorbent article of claim 1, wherein the second attachment region comprises a first adhesive disposed throughout the low-strength attachment zone.

3. The absorbent article of claim 2, wherein the second attachment region comprises a second adhesive disposed throughout the high-strength attachment zone, and wherein the second adhesive is different than the first adhesive.

4. The absorbent article of claim 3, wherein the first adhesive has a drop time of less than 4 hours in the Static Shear Test Method, and wherein the second adhesive has a drop time of greater than or equal to 4 hours in the Static Shear Test Method.

5. The absorbent article of claim 2, wherein the first adhesive is disposed throughout at least a portion of the high-strength attachment zone.

6. The absorbent article of claim 2, wherein the first adhesive is disposed throughout the entire high-strength attachment zone.

7. The absorbent article of claim 2, wherein the high strength attachment zone is comprised of a plurality of bonds.

8. The absorbent article of claim 7, wherein a bonded surface area of the bonds within the high-strength attachment zone comprises between about 25% and about 75% of the surface area of the high-strength attachment zone.

9. The absorbent article of claim 1, wherein the first peel strength is less than or equal to 4 N, according to the Angled Peel Test Method, and wherein the second peel strength is greater than or equal to 8 N, according to the Angled Peel Test Method.

10. The absorbent article of claim 1, wherein the high-strength attachment zone is disposed proximate one of the attachment region longitudinal side edges.

11. The absorbent article of claim 1, wherein the second attachment region comprises a first high-strength attachment zone and a second high-strength attachment zone, the first high-strength attachment zone disposed proximate a first attachment region longitudinal side edge and the second high-strength attachment zone disposed proximate a second attachment region longitudinal side edge.

12. The absorbent article of claim 1, wherein the attachment region bottom edge further comprises at least one recess, wherein:
the at least one recess comprises a first recess side edge, a second recess side edge, and a recessed edge,
the first recess side edge is located a distance between 15% and 40% of the overall attachment region width from the first attachment region longitudinal side edge, and
the second recess side edge is located a distance between 15% and 40% of the overall attachment region width from the second attachment region longitudinal side edge.

13. The absorbent article of claim 11, wherein the second attachment region comprises a first high-strength attachment zone and a second high-strength attachment zone, the first high-strength attachment zone disposed proximate the attachment region bottom edge and the second high-strength attachment zone disposed proximate the attachment region top edge.

14. An absorbent article including front region, a crotch region, and a rear region, the article having a first side edge and a second side edge and further comprising:
an absorbent insert comprising an outer cover, a liner, and an absorbent core disposed between the outer cover and the liner;
a first waist panel coupled to the absorbent insert throughout a first attachment region; and
a second waist panel coupled to the absorbent insert throughout a second attachment region and comprising a weakened region, the second waist panel being coupled to the first waist panel proximate the first side edge of the absorbent article and the second side edge of the absorbent article,
wherein the second attachment region comprises an attachment region top edge, an attachment region bottom edge, attachment region longitudinal side edges, and overall attachment region area, and
wherein the second attachment region further comprises an adhesive-less region extending in a longitudinal direction and wherein the weakened region overlaps the adhesive-less region, and wherein the adhesive-less region has an adhesive-less region width, the adhesive-less region width being between about 8 mm and about 22 mm.

15. The absorbent article of claim 14, wherein the adhesive-less region has an adhesive-less region width, the adhesive-less region width being between about 12 mm and about 18 mm.

16. The absorbent article of claim 14, wherein the second attachment region further comprises a low-strength attachment zone and a high-strength attachment zone, the high-strength attachment zone being disposed proximate the attachment region bottom edge,
wherein a peel strength of the low-strength attachment zone is less than or equal to 4 N, according to the Angled Peel Test Method, and
wherein a peel strength of the high-strength attachment zone is greater than or equal to 8 N, according to the Angled Peel Test Method.

17. An absorbent article including front region, a crotch region, and a rear region, the article having a first side edge and a second side edge and further comprising:
an absorbent insert comprising an outer cover, a liner, and an absorbent core disposed between the outer cover and the liner;
a first waist panel coupled to the absorbent insert throughout a first attachment region; and
a second waist panel coupled to the absorbent insert throughout a second attachment region and comprising a weakened region, the second waist panel being coupled to the first waist panel proximate the first side edge of the absorbent article and the second side edge of the absorbent article,
wherein the second attachment region comprises an attachment region top edge, an attachment region bottom edge, attachment region longitudinal side edges, and overall attachment region area,
wherein the second attachment region further comprises a low-strength attachment zone, a first high-strength attachment zone, and a second high-strength attachment zone, the first high-strength attachment zone and the second high-strength attachment zone each being disposed proximate the attachment region bottom edge and one of the attachment region longitudinal side edges,
wherein the low-strength attachment zone has a first peel strength and the high-strength attachment zone has a second peel strength, the second peel strength being greater than the first peel strength, and wherein the first high-strength attachment zone and the second high-strength attachment zone each has a high-strength attachment zone area that is between about 0.5% and about 10% of the overall attachment region area.

18. The absorbent article of claim 17, wherein the peel strength of the low-strength attachment zone is between about 1.5 N and about 4 N, according to the Angled Peel Test Method.

19. The absorbent article of claim 17, wherein the peel strength of the high-strength attachment zone is greater than or equal to 8 N, according to the Angled Peel Test Method.

* * * * *